(12) United States Patent
Wipf et al.

(10) Patent No.: US 7,528,174 B2
(45) Date of Patent: May 5, 2009

(54) SELECTIVE TARGETING AGENTS FOR MITOCHONDRIA

(75) Inventors: Peter Wipf, Pittsburgh, PA (US); Jingbo Xiao, Pittsburgh, PA (US); Mitchell P. Fink, Pittsburgh, PA (US); Valerian E. Kagan, Pittsburgh, PA (US); Yulia Y. Tyurina, Pittsburgh, PA (US)

(73) Assignee: University of Pittsburgh-Of The Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 11/465,162

(22) Filed: Aug. 17, 2006

(65) Prior Publication Data

US 2007/0161573 A1 Jul. 12, 2007

Related U.S. Application Data

(60) Provisional application No. 60/757,044, filed on Jan. 6, 2006.

(51) Int. Cl.
*A61K 38/05* (2006.01)
*A61K 38/06* (2006.01)
*A61K 38/08* (2006.01)
*A61K 31/00* (2006.01)

(52) U.S. Cl. ............................ 514/645; 514/17; 514/18; 514/19

(58) Field of Classification Search ........................ None
See application file for complete search history.

(56) References Cited

U.S. PATENT DOCUMENTS

| | | | |
|---|---|---|---|
| 6,331,532 B1 | 12/2001 | Murphy et al. | |
| 2005/0107366 A1 | 5/2005 | Carney et al. | |
| 2005/0169904 A1 | 8/2005 | Payne | |
| 2005/0245487 A1 | 11/2005 | Murphy et al. | |

OTHER PUBLICATIONS

Wipf et al., "Mitochondrial targeting of selective electron scavengers: synthesis and biological analysis of hemigramicidin-TEMPO conjugates," J. Am. Chem. Soc., 2005, 127, 12460-1.*
Niccolai et al., "An investigation of the mechanisms of nitroxide-induced proton relaxation enhancements in biopolymers," J. Phys. Chem., 1994, 88, 5689-5692.*
Zhao et al. "Cell-permeable peptide antioxidants targeted to inner mitochondrial membrane inhibit mitochondrial swelling, oxidative cell death, and reperfusion injury.," J. Biol. Chem., 2004, 279, 34682-90.*
Schnackenberg & Wilcox, Two-Week Administration of Tempol Attenuates Both Hypertension and Renal Excretion of 8-Iso Prostaglandin F2, Hypertension, 1999, 33, 424-428.*
Hahn et al., Tempol, a Stable Free Radical, Is a Novel Murine Radiation Protector, Cancer Research, 1992, 52, 1750-1753.*
Nishiyama et al., Systemic and Regional Hemodynamic Responses to Tempol in Angiotensin II-Infused Hypertensive Rats, Hypertension, 2001, 37, 77-83.*

McDonald et al., Tempol reduces infarct size in rodent models of regional myocardial ischemia and reperfusion, Free Radical Biology and Medicine, 1999, 27, 493-503.*
Cuzzocrea et al., Effects of tempol, a membrane-permeable radical scavenger, in a gerbil model of brain injury, Brain Research, 2000, 875, 96-106.*
Liaw et al., Effects Of A Membrane-Permeable Radical Scavenger, Tempol, On Intraperitoneal Sepsis-Induced Organ Injury In Rats, Shock, 2005, 23, 88-96.*
Thiemermann, Membrane-permeable radical scavengers (tempol) for shock, ischemia-reperfusion injury and inflammation, Crit. Care Med., 2003, 31, S76-S84.*
Abashkin YG, Burt SK. (salen)MnIII compounds as nonpeptidyl mimics of catalase. Mechanism-based tuning of catalase activity: a theoretical study. Inorg Chem. Mar. 7, 2005;44(5):1425-32.
Baker RD, et al. Polarized Caco-2 cells. Effect of reactive oxygen metabolites on enterocyte barrier function. Dig Dis Sci. Mar. 1995; 40(3):510-8.
Banan A, et al. Activation of delta-isoform of protein kinase C is required for oxidant-induced disruption . . . J Pharmacol Exp Ther. Oct. 2002;303(1):17-28.
Batinic-Haberle I, et al. New PEG-ylated Mn(III) porphyrins approaching catalytic activity of SOD enzyme. Dalton Trans. Jan. 28, 2006;(4):617-24.
Bottcher CFJ, et al. A rapid and sensitive sub-micro phosphorous determination. Anal Chim Acta. 1961 24, 203-204.
Butler MS, Buss AD. Natural products—the future scaffolds for novel antibiotics? Biochem Pharmacol. Mar. 30, 2006;71(7):919-29.
Cairns CB. Rude unhinging of the machinery of life: metabolic approaches to hemorrhagic shock. Curr Opin Crit Care. Dec. 2001;7(6):437-43.

(Continued)

*Primary Examiner*—Cecilia Tsang
*Assistant Examiner*—Christina Marchetti Bradley
(74) *Attorney, Agent, or Firm*—Hirshman Law; Jesse A. Hirshman

(57) ABSTRACT

Compositions and methods are disclosed for treating an illness that is caused or associated with cellular damage or dysfunction which is caused by excessive mitochondrial production of reaction oxygen species (ROS). Compositions which act as mitochondria-selective targeting agents using specific structural signaling features recognizable by cells as mitochondrial targeting sequences are discussed. A method for delivering these agents effectively into cells and mitochondria where they act as electron scavengers by way of certain targeting sequences is also disclosed. Mitochondria dysfunction and cell death by way of apoptosis is inhibited as a result of the ROS-scavenging activity, thereby increasing the survival rate of the patient. In a preferred embodiment, the compositions and methods may be administered therapeutically in the field to patients with profound hemorrhagic shock so that survival could be prolonged until it is feasible to obtain surgical control of the bleeding vessels.

17 Claims, 10 Drawing Sheets

OTHER PUBLICATIONS

Clement AM et al. Wild-type nonneuronal cells extend survival of SOD1 mutant motor neurons in ALS mice. Science. Oct. 3, 2003;302(5642):113-7.

Dolder M, et al. Mitochondrial creatine kinase in contact sites: interaction with porin and adenine nucleotide translocase . . . Biol Signals Recept. Jan.-Apr. 2001;10(1-2):93-111.

Edmonds MK, Abell AD. Design and synthesis of a conformationally restricted trans peptide isostere based on the bioactive conformations . . . J Org Chem. Jun. 1, 2001;66(11):3747-52.

Epperly MW, et al. Manganese superoxide dismutase (SOD2) inhibits radiation induced apoptosis by stabilization of the mitochondrial membrane. Rad Res 2002; 157: 568-577.

Folch J, et al. A simple method for the isolation and purification of total lipids from animal tissues. J. Biol. Chem. 1957 226: 497-509.

Gibson SE, Lecci C. Amino acid derived macrocycles—an area driven by synthesis or application? Angew Chem Int Ed Engl. Feb. 20, 2006;45(9):1364-77.

Hahn SM, et al. Mn(III)-Desferrioxamine superoxide dismutase-mimic: alternative modes of action. Arch. Biochem. Biophy. Jul. 1991;288(1):215-219.

Han X, et al. Proinflammatory cytokines cause NO*-dependent and -independent changes in expression and localization of tight junction proteins . . . Shock. Mar. 2003;19(3):229-37.

He H. Mannopeptimycins, a novel class of glycopeptide antibiotics active against gram-positive bacteria. Appl Microbiol Biotechnol. Jun. 2005;67(4):444-52.

Imai H, et al. Protection from inactivation of the adenine nucleotide translocator during hypoglycaemia-induced apoptosis by mitochondrial . . . Biochem J. May 1, 2003;371(Pt 3):799-809.

Itami C, et al. Superoxide dismutase mimetic activities of metal complexes of . . . Biochem Biophys Res Commun. Dec. 15, 1993;197(2):536-41.

Iverson SL, Orrenius S. The cardiolipin-cytochrome c interaction and the mitochondrial regulation of apoptosis. Arch Biochem Biophys. Mar. 1, 2004;423(1):37-46.

Kagan VE, et al. A role for oxidative stress in apoptosis: oxidation and externalization of phosphatidylserine is required . . . J Immunol. Jul. 1, 2002;169(1):487-99.

Kagan VE, et al. Cytochrome c acts as a cardiolipin oxygenase required for release of proapoptotic factors. Nat Chem Biol. Sep. 2005;1(4):223-32.

Kagan VE, et al. Oxidative lipidomics of apoptosis: redox catalytic interactions of cytochrome c with cardiolipin and phosphatidylserine. Free Radic Biol Med. Dec. 15, 2004;37(12):1963-85.

Kanai AJ, et al. Manganese superoxide dismutase gene therapy protects against irradiation-induced cystitis. Am J Physiol Renal Physiol. Dec. 2002;283(6):F1304-12.

Kanai A, et al. Differing roles of mitochondrial nitric oxide synthase in cardiomyocytes and urothelial cells. Am J Physiol Heart Circ Physiol. Jan. 2004;286(1):H13-21.

Kanai AJ, et al. Identification of a neuronal nitric oxide synthase in isolated cardiac mitochondria using electrochemical detection. Proc Natl Acad Sci U S A. Nov. 20, 2001;98(24):14126-31.

Kanai A, Peterson J. Function and regulation of mitochondrially produced nitric oxide in cardiomyocytes. Am J Physiol Heart Circ Physiol. Jan. 2004;286(1):H11-2.

Kelso GF, et al P. Selective targeting of a redox-active ubiquinone to mitochondria within cells: antioxidant and antiapoptotic properties. J Biol Chem. Feb. 16, 2001;276(7):4588-96.

Kentner R, et al. Early antioxidant therapy with Tempol during hemorrhagic shock increases survival in rats. J Trauma. Nov. 2002;53(5):968-77.

Konorev EA, et al. Cell-permeable superoxide dismutase and glutathione peroxidase mimetics afford superior protection against . . . Arch Biochem Biophys. Aug. 15, 1999;368(2):421-8.

Lee DL, Hodges RS. Structure-activity relationships of de novo designed cyclic antimicrobial peptides based on gramicidin S. Biopolymers. 2003;71(1):28-48.

Macias CA, et al. Treatment with a novel hemigramicidin-TEMPO conjugate prolongs survival in a rat model of lethal hemorrhagic shock. Ann Surg. Feb. 2007;245(2):305-14.

Nicolas P, et al. Molecular strategies in biological evolution of antimicrobial peptides. Peptides. Nov. 2003;24(11):1669-80.

Olcott AP, et al. A salen-manganese catalytic free radical scavenger inhibits type 1 diabetes and islet allograft rejection. Diabetes. Oct. 2004;53(10):2574-80.

Payne JW, et al. Conformer profiles and biological activities of peptides. Curr Org Chem. 2002, 6: 1221-46.

Pieper GM, et al. Protective mechanisms of a metalloporphyrinic peroxynitrite decomposition catalyst . . . J Pharmacol Exp Ther. Jul. 2005;314(1):53-60.

Porter EA, et al. Mimicry of host-defense peptides by unnatural oligomers: antimicrobial beta-peptides. J Am Chem Soc. Jun. 26, 2002;124(25):7324-30.

Raguse TL, et al. Structure-activity studies of 14-helical antimicrobial beta-peptides: probing the relationship between conformational stability . . . J Am Chem Soc. Oct. 30, 2002;124(43):12774-85.

Shidoji Y, et al. Loss of molecular interaction between cytochrome c and cardiolipin due to lipid peroxidation. Biochem Biophys Res Commun. Oct. 22, 1999;264(2):343-7.

Tamaki M, et al. CD spectra and cyclization of linear pentapeptides as gramicidin S precursors with a benzyloxycarbonyl group on the side chain . . . Bull Chem Soc Jpn. 1993 66(10): 3113-15.

Tuominen EK, et al. Phospholipid-cytochrome c interaction: evidence for the extended lipid anchorage. J Biol Chem. Mar. 15, 2002;277(11):8822-6.

Wade D, et al. Antibiotic properties of novel synthetic temporin A analogs and a cecropin A-temporin A hybrid peptid. Protein Pept Lett. Dec. 2002;9(6):533-43.

Wattanasirichaigoon S, et al. Effect of mesenteric ischemia and reperfusion or hemorrhagic shock on intestinal mucosal permeability and ATP content in rats. Shock. Aug. 1999;12(2):127-33.

Wipf P, Xiao J. Convergent approach to (E)-alkene and cyclopropane peptide isosteres. Org Lett. Jan. 6, 2005;7(1):103-6.

Wipf P, et al. Mitochondrial targeting of selective electron scavengers: synthesis and biological analysis of hemigramicidin-TEMPO conjugates. J Am Chem Soc. Sep. 14, 2005;127(36):12460-1.

Wipf P, et al. Methyl- and (Trifluoromethyl)alkene Peptide Isosteres: Synthesis and Evaluation of Their Potential as beta-Turn Promoters and Peptide . . . J Org Chem. Sep. 4, 1998;63(18):6088-6089.

Wipf P, et al. Synthesis of chemoreversible prodrugs of ara-C with variable time-release profiles. Biological evaluation of their apoptotic activity. Bioorg Med Chem. Oct. 1996;4(10):1585-96.

Wood PL, et al. Neurotoxicity of reactive aldehydes: the concept of "aldehyde load" as demonstrated by neuroprotection with hydroxylamines. Brain Res. Jun. 20, 2006;1095(1):190-9.

Xiao J, et al. Electrostatic versus steric effects in peptidomimicry: synthesis and secondary structure analysis of gramicidin S analogues with (E)-alkene . . . J Am Chem Soc. Apr. 27, 2005;127(16):5742-3.

Yamamoto S, et al R. Anti-tumor promoting action of phthalic acid mono-n-butyl ester cupric salt, a biomimetic superoxide dismutase. Carcinogenesis. May 1990;11(5):749-54.

Yang R, et al. Ethyl pyruvate modulates inflammatory gene expression in mice subjected to hemorrhagic shock. Am J Physiol Gastrointest Liver Physiol. Jul. 2002;283(1):G212-21.

* cited by examiner

SELECTIVE TARGETING AGENTS FOR MITOCHONDRIA

CROSS-REFERENCE TO RELATED APPLICATIONS

This application claims the benefit of U.S. Provisional Application No. 60/757,044 entitled "Gramicidin S Based Mitrochondrial Targeting Agents" filed on Jan. 6, 2006. The disclosure of U.S. Provisional Application No. 60/757,044 is hereby incorporated into the present application by reference.

GOVERNMENT SUPPORT

The present invention was supported by a DARPA government contract no. W81XWH-05-2-0026 and a U.S. Public Health Service National Institutes of Health grant, no. GM067082. The federal government may have certain rights therein.

BACKGROUND OF THE INVENTION

1. Field of the Invention

The present invention relates to compositions and methods for providing mitochondria-selective targeting agents. Specifically, this invention focuses on compositions and methods of Gramicidin-S peptidyl conjugates for selective targeting of therapeutic agents to mitochondria. Furthermore, this invention focuses on compositions and methods of Gramicidin-S peptidyl TEMPO conjugates, particularly synthetic Gramicidin S-peptidyl TEMPO (2,2,6,6-tetramethylpiperidine-N-oxyl) conjugates.

2. Description of the Prior Art

Cells typically undergo some degree of oxidative stress by way of generating reactive oxygen species ("ROS"). Specifically, the cellular respiration pathway generates ROS within the mitochondrial membrane of the cell, see Kelso et al., *Selective Targeting of a Redox-active Ubiquinone to Mitochondria within Cells: Antioxidant and Antiapoptotic Properties*, J. OF BIOL. CHEM. 276:4588 (2001). Reactive oxygen species include free radicals, reactive anions containing oxygen atoms, and molecules containing oxygen atoms that can either produce free radicals or are chemically activated by them. Specific examples include superoxide anion, hydroxyl radical, and hydroperoxides.

Naturally occurring enzymes, such as superoxide dismutase ("SOD") and catalase salvage ROS radicals to allow normal metabolic activity to occur.

Significant deviations from cell homeostasis, such as hemorrhagic shock, lead to an oxidative stress state, thereby causing "electron leakage" from the mitochondrial membrane. Said "electron leakage" produces an excess amount of ROS which the cell's natural antioxidants cannot compensate for. Specifically, SOD cannot accommodate the excess production of ROS associated with hemorrhagic shock which ultimately leads to premature mitochondria dysfunction and cell death via apoptosis, see Kentner et al., *Early Antioxidant Therapy with TEMPOL during Hemmorhagic Shock Increases Survival in Rats*, J. OF TRAUMA® INJURY, INFECTION, AND CRITICAL CARE, 968 (2002).

Cardiolipin ("CL") is an anionic phospholipids exclusively found in the inner mitochondrial membrane of eukaryotic cells, see Iverson, S. L. and S. Orrenius, *The cardiolipin-cytochrome c interaction and the mitochondrial regulation of apoptosis*, ARCH. BIOCHEM. BIOPHYS. 423:37-46 (2003).

Under normal conditions, the pro-apoptotic protein cytochrome c is anchored to the mitochondrial inner membrane by binding with CL, see Tuominen, E. K. J., et al. *Phospholipid cytochrome c interaction: evidence for the extended lipid anchorage*, J. BIOL. CHEM., 277:8822-8826 (2002). The acyl moieties of CL are susceptible to peroxidation by reactive oxygen species. When ROS are generated within mitochondria in excess quantities, cytochrome c bound to CL can function as an oxidase and induces extensive peroxidation of CL in the mitochondrial membrane, see Kagan, V. E. et al., *Cytochrome c acts as a cardiolipin oxygenase required for release of proapoptotic factors*, NATURE CHEM. BIOL. 1:223-232 (2005); also Kagan, V. E. et al., *Oxidative lipidomics of apoptosis: redox catalytic interactions of cytochrome c with cardiolipin and phosphatidylserine*, FREE RAD. BIOL. MED. 37:1963-1985 (2005).

The peroxidation of the CL weakens the binding between the CL and cytochrome c, see Shidoji, Y. et al., *Loss of molecular interaction between cytochrome c and cardiolipin due to lipid peroxidation*, BIOCHEM. BIOPHYS. RES. COMM. 264: 343-347 (1999). This leads to the release of the cytochrome c into the mitochondrial intermembrane space, inducing apoptotic cell death.

Further, the peroxidation of CL has the effect of opening the mitochondrial permeability transition pore "MPTP"), see Dolder, M. et al., *Mitochondrial creatine kinase in contact sites: Interaction with porin and adenine nucleotide translocase, role in permeability transition and sensitivity to oxidative damage*, BIOL. SIGNALS RECEPT., 10:93-111 (2001); also Imai, H. et al., *Protection from inactivation of the adenine nucleotide translocator during hypoglycaemia-induced apoptosis by mitochondrial phospholipid hydroperoxide glutathione peroxidase*, BIOCHEM. J., 371:799-809 (2003). Accordingly, the mitochondrial membrane swells and releases the cytochrome c into the cytosol. Excess cytochrome c in the cytosol leads to cellular apostosis, see Iverson, S. L. et al. *The cardiolipin-cytochrome c interaction and the mitochondrial regulation of apoptosis*, ARCH. BIOCHEM. BIOPHYS. 423:37-46 (2003).

Moreover, mitochondrial dysfunction and cell death may ultimately lead to multiple organ failure despite ef resuscitative efforts or supplemental oxygen supply, see Cairns, Charles M D, *Rude Unhinging of the Machinery of Life: Metabolic approaches to hemorrhagic Shock*, CURRENT OPINION IN CRITICAL CARE, 7:437 (2001). Accordingly, there is a need in the art for an antioxidant mimic similar to SOD which scavenges the ROS, thereby reducing oxidative stress. Reduction of oxidative stress delays, even inhibits, physiological conditions that otherwise might occur, such as hypoxia.

Also, there is also a need to improve the permeability of antioxidants' penetration of the cellular membrane. One of the limitations of SOD is that it cannot easily penetrate the cell membrane. However, nitroxide radicals, such as TEMPO (2,2,6,6-tetramethylpiperidine-N-oxyl) and its derivatives, have been shown to penetrate the cell membrane better than SOD. Further, nitroxide radicals like TEMPO prevent the formation of ROS, particularly superoxide, due to their reduction by the mitochondrial electron transport chain to hydroxylamine radical scavengers, see Wipf, P. et al., *Mitochondrial targeting of selective electron scavengers: synthesis and biological analysis of hemigramicidin-TEMPO conjugates*, J. AM. CHEM. SOC. 127:12460-12461. Accordingly, selective delivery of TEMPO derivatives may lead to a therapeutically beneficial reduction of ROS and may delay or inhibit cell death due to the reduction of oxidative stress on the cell.

This selective delivery may be accomplished by way of a number of different pathways—i.e., a biological or chemical moiety has a specific targeting sequence for penetration of the cell membrane, ultimately being taken up by the mitochondrial membrane. Selective delivery of a nitroxide SOD mimic into the mitochondrial membrane has proven difficult. Accordingly, there is a need in the art for effective selective delivery of TEMPO antioxidant derivatives that specifically target the cell membrane and, more specifically, the mitochondrial membrane to help reduce the ROS species. Said antioxidants also help prevent cellular and mitochondria apoptotic activity which often results due to excessive ROS species, see Kelso et al., *Selective Targeting of a Redox-active Ubiquinone to Mitochondria within Cells: Antioxidant and Antiapoptotic Properties*, J. OF BIOL. CHEM., 276: 4588 (2001).

U.S. Patent Application 2005/0169904 discloses a conjugate which comprises the following: (i) a mitochondrial membrane-permeant peptide; (ii) a mitochondrial-active agent or compound of interest such as a detectable group or compound, an active mitochondrial protein or peptide, nucleic acids, drug or signaling agent; and, (iii) a mitochondrial targeting sequence linking said mitochondrial membrane-permeant peptide and said active mitochondrial protein or peptide. The targeting sequence of the conjugate is cleaved within the mitochondrial matrix, not within the cellular cytoplasm of a target cell into which said mitochondrial-active agent or compound is to be delivered. Methods of use of these compounds and agents are also disclosed within the publication. A disadvantage of this methlolodogy is that it requires cleavage of the peptide sequence in order to release the active agent.

U.S. Pat. No. 6,331,532 and US Patent Application 2005/0245487 A1 disclose mitochondrially targeted antioxidant compounds. The compound comprises a lipophilic cation covalently bonded to an antioxidant moiety. Pharmaceutical compositions containing the mitochondrially targeted antioxidant compounds, and methods of therapy or prophylaxis of patients who would benefit from reduced oxidative stress are disclosed. This methodology relies on ionic or lipophilic interactions and is less selective than the present invention.

US Patent Application 2005/0107366 A1 discloses a pharmaceutical composition that is covalently bound to a nontoxic spin trapping compound. Spin trapping compositions generally have been known to be effective in treating a variety of disorders. Spin trapping compounds are molecules that have an unpaired electron (i.e., paramagnetic), form a stable compound or complex with a free radical, and lack cytotoxicity. One example of a spin trapping compound which is provided is TEMPO. These spin trapping compounds, such as TEMPO, provide a unique signal that can be measured by electron spin spectroscopy (ESR). Since an effective mitochondrial-targeting sequence is not used, this approach is not as efficient as the present invention.

TEMPO and its derivatives are antioxidants that have been shown to improve physiologic variables after induced hemmorhagic shock, such as heart rate, systolic blood pressure, acid-base balance, serum antioxidant status, and survival time, see Kentner et al., *Early Antioxidant Therapy with TEMPOL during Hemmorhagic Shock Increases Survival in Rats*, J. OF TRAUMA® INJURY, INFECTION, AND CRITICAL CARE, 968 (2002). In general, effective levels of administered TEMPO are too high to accomplish therapeutic effects.

Therefore, in spite of the foregoing prior art, there remains a very real need for TEMPO-related compositions and methods for effectively treating a condition that is caused by excessive mitochondrial production of reaction oxygen species (ROS) in the mitochondrial membrane.

SUMMARY OF THE INVENTION

The present invention has met the herein before described need by providing compositions and methods as disclosed for treating a condition, including a disease or other medical condition, which is caused by excessive mitochondrial production of reaction oxygen species (ROS) in the mitochondrial membrane. In a preferred embodiment, the compositions are conjugates of Gramicidin S peptidyl fragments and TEMPO derivatives. The Gramicidin S peptidyl fragment is either Gramicidin S or a hemigramicidin fragment. In a further embodiment, a hemigramicidin (i.e., a fragmented version of Gramicidin S with additional functional groups) motif with an amide bond isostere constitute the Gramicidin moiety of the TEMPO-peptidyl conjugate. In a preferred embodiment, the amide bond isostere is an (E)-alkene moiety.

Yet another embodiment provides a method for delivering these TEMPO-peptidyl conjugates effectively into cells to mitochondria. Specifically, the peptidyl conjugates comprise a targeting sequence which is recognizable by the mitochondria and also permeable to the mitochondrial membrane. The peptidyl conjugate thereby "anchors" the TEMPO "payload" into the mitochondrial membrane whereby the TEMPO acts as an electron scavenger of the reactive oxygen species present within the membrane. Accordingly, the electron scavenging activity of the TEMPO helps resist mitochondrial dysfunction and cell death.

Another preferred embodiment provides a method for therapeutically administering the TEMPO-peptidyl conjugate to patients with hemorrhagic shock to help prolong survival until it is feasible to obtain control of the bleeding vessels of the patient. In yet another related embodiment, a method for therapeutically administering the TEMPO-peptidyl conjugate to patients with hemorrhagic shock to help prolong survival until it is feasible to obtain control of the bleeding vessels of the patient, in spite of a lack of resuscitation with blood or other non-sanguinous fluids. In still yet another related embodiment, a method for therapeutically administering the TEMPO-peptidyl conjugate to patients with hemorrhagic shock to help prolong survival until it is feasible to obtain control of the bleeding vessels of the patient, in spite of hypotension.

An object of this invention is to provide compositions which effectively act as mitochondria-selective targeting agents to help anchor an attached moiety (cargo) into the mitochondria membrane.

Another object of this invention is to provide a method for delivering these agents effectively into cells and mitochondria where they act as electron scavengers. Yet another object of the invention is to provide a method which provides agents that exert protection against mitochondrial dysfunction and cell apoptosis.

Yet another object of this invention is to prolong the survival of a patient that has suffered hemorrhagic shock. A related object of this invention is to prolong the survival of a patient that has suffered hemorrhagic shock and has not been resuscitated with blood or non-sanguinous other fluids. Yet another related object of this invention is to prolong the survival of a patient that has suffered hemorrhagic shock and is hypotensive.

Still another object of the invention is to provide a composition and method for treating a condition, including a disease or other medical condition, which is the result from excessive mitochondrial production of reaction oxygen species (ROS).

Yet another object of this invention is to provide a method for administering the composition to patients with a condition, including a disease or an illness, which is the result from excessive mitochondrial production of reaction oxygen species (ROS).

These and other objects of the invention will be more fully understood from the following detailed description of the invention on reference to the illustrations and table appended hereto.

BRIEF DESCRIPTION OF THE DRAWINGS

FIG. 1A shows TEMPOL.

FIG. 1B shows a dipeptidic TEMPO analog—XJB-5-208.

FIG. 1C shows a hemigramicidin-TEMPO conjugate—XJB-5-125.

FIG. 1D shows a hemigramicidin compound that does not have the TEMPO moiety—XJB-5-127.

FIG. 1E shows a hemigramicidin-TEMPO conjugate—XJB-5-131.

FIG. 1F shows a hemigramicidin compound that does not have the TEMPO moiety—XJB-5-133.

FIG. 1G shows a hemigramicidin-TEMPO conjugate—XJB-5-197.

FIG. 1H shows a hemigramicidin compound that does not have the TEMPO moiety—XJB-5-194.

FIG. 4A shows an FD4 read-out of TEMPOL which is used as a "positive control" for the gut mucosal protection assay.

FIG. 4B shows an FD4 read-out of TEMPO conjugate XJB-5-208 reflecting gut mucosal protection.

FIG. 4C shows an FD4 read-out of XJB-5-125 which has the TEMPO payload, but fails to provide protection against gut barrier dysfunction induced by hemorrhage.

FIG. 4D shows an FD4 read-out of XJB-5-127 which lacks the TEMPO payload and fails to provide protection against gut barrier dysfunction induced by hemorrhage.

FIG. 4E shows an FD4 read-out of TEMPO conjugate XJB-5-131 reflecting gut mucosal protection.

FIG. 4F shows an FD4 read-out of XJB-5-133 which lacks the TEMPO payload even though it possesses the same hemigramicidin mitochondria targeting moiety as the most active compound, XJB-5-131.

FIG. 4G shows an FD4 read-out of XJB-5-197 which has the TEMPO payload, but fails to provide protection against gut barrier dysfunction induced by hemorrhage.

FIG. 4H shows an FD4 read-out of XJB-5-194 which lacks the TEMPO payload and fails to provide protection against gut barrier dysfunction induced by hemorrhage.

FIG. 5A is a graphical representation of superoxide production based upon mean fluorescence intensity from 10,000 ileal cells.

FIG. 5B is a graphical representation of phosphatidylserine (PS) externalization as indicated by the percentage of annexin V-positive cells.

FIG. 5C is a graphical representation of caspase-3 activity as indicated by amount of its specific substrate present, Z-DVED-AMC, in nmol/mg protein.

FIG. 5D is a graphical representation of DNA fragmentation as indicated by propidium iodide fluorescence.

FIG. 5E is a graphical representation of PS externalization at different concentrations of the compound 5a.

FIG. 5F is a graphical representation of adenosine triphosphate (ATP) levels in mitochondria in the presence or absence of 5a or 2-deoxyglucose.

FIG. 6A is a graphical representation of the peroxidation of phosphatidylcholine (PC).

FIG. 6B is a graphical representation of peroxidation activity with respect to phosphatidylethanolamine (PE).

FIG. 6C is a graphical representation of peroxidation activity with respect to phosphatidylserine (PS).

FIG. 6D is a graphical representation of peroxidation activity with respect to cardiolipin (CL).

DESCRIPTION OF THE PREFERRED EMBODIMENTS

Figure 1:
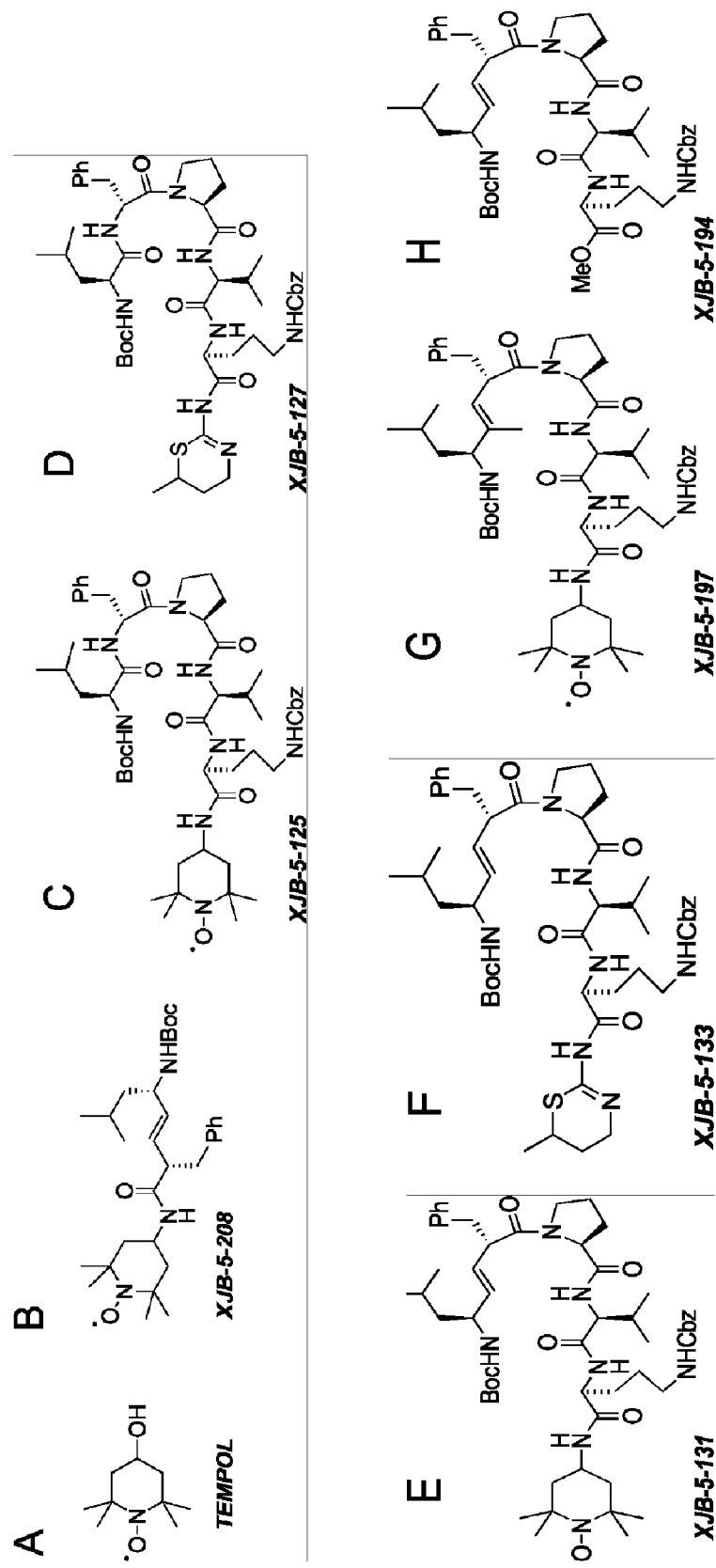
FIG. 1 depicts the chemical structure of TEMPOL and the seven hemigramicidin derivative compounds.

As used herein, the term "patient" refers to members of the animal kingdom including but not limited to human beings.

As used herein, the term "reactive oxygen species" ("ROS") includes, but is not limited to, superoxide anion, hydroxyl, and hydroperoxide radicals.

While the generation of ROS in small amounts is a typical byproduct of the cellular respiration pathway, certain conditions, including a disease or other medical condition, may occur in the patient when the amount of ROS is excessive to the point where natural enzyme mechanisms cannot scavenge the amount of ROS being produced.

The present invention provides compositions and methods that scavenge reactive oxygen species ("ROS") that are present within the mitochondrial membrane of the cell. These compositions and methods have the utility of being able to scavenge an excess amount of ROS being produced that naturally occurring enzymes SOD and catalase, among others, cannot cope with.

In one aspect of the invention, compounds possessing electron scavenger properties similar to SOD and catalase are disclosed. In another aspect of the invention, methods for targeting the mitochondria of the cell are discussed.

In one embodiment of the present invention, the compositions were derived from a conjugate form of 4-amino-TEMPO and peptidyl fragments of Gramicidin S. As is known to one ordinarily skilled in the art, Gramicidin S is a well-known antibiotic and has a high affinity to bacterial membranes. Further, bacteria and mitochondria are structurally quite similar. Accordingly, it was found that appropriately folded peptidyl fragments of Gramicidin S have a high affinity for mitochondria and permeate through the cytoplasm membrane of the cell. Therefore, targeting of mitochondria by way of Gramicidin S peptidyl fragments proved to be useful. In another embodiment, the compositions were derived from a conjugate form of TEMPOL and peptidyl fragments of Gramicidin S.

Accordingly, using the Gramicidin S peptidyl fragments and alkene isosteres as "anchors," the TEMPO "payload" could be guided into the mitochondrial membrane.

In one embodiment, the Leu-$^D$Phe-Pro-Val-Orn fragment of hemigramicidin may advantageously be used as a targeting sequence. The β-turn motif of the Gramicidin-S fragment directs most of the polar functionality of the peptide strand into the core; the amino functional groups of Leu and Orn are acylated so that cytotoxicity of gramicidin S is reduced.

Alkene isosteres such as (E)-alkene isosteres of Gramicidin S (i.e., hemigramicidin) were used as part of the targeting sequence. See FIG. 2 for the synthetic pathway for (E)-alkene isosteres and reference number 2 for the corresponding chemical structure. First, hydrozirconation of alkyne (FIG. 2, compound 1) with $Cp_2ZrHCl$ followed by transmetalation to $Me_2Zn$ and the addition of the N-Boc functional group using N-Boc-isovaleraldimine. The product afforded diastereomeric allylic amides, which were separated after desilylation and acetylation. The resulting compound (not shown) was then worked up using a solution of tetrabutylammonium fluoride (TBAF) and diacetyl ether with a 74% yield. This compound (not shown) was then treated with diacetyl ether, triethylamine (TEA), and 4-(dimethylamino) pyridine (DMAP) with a 94% yield. Finally, this compound was worked up with $K_2CO_3$ in methanol to yield the (E)-alkene, depicted as compound 2.

Figure 2:
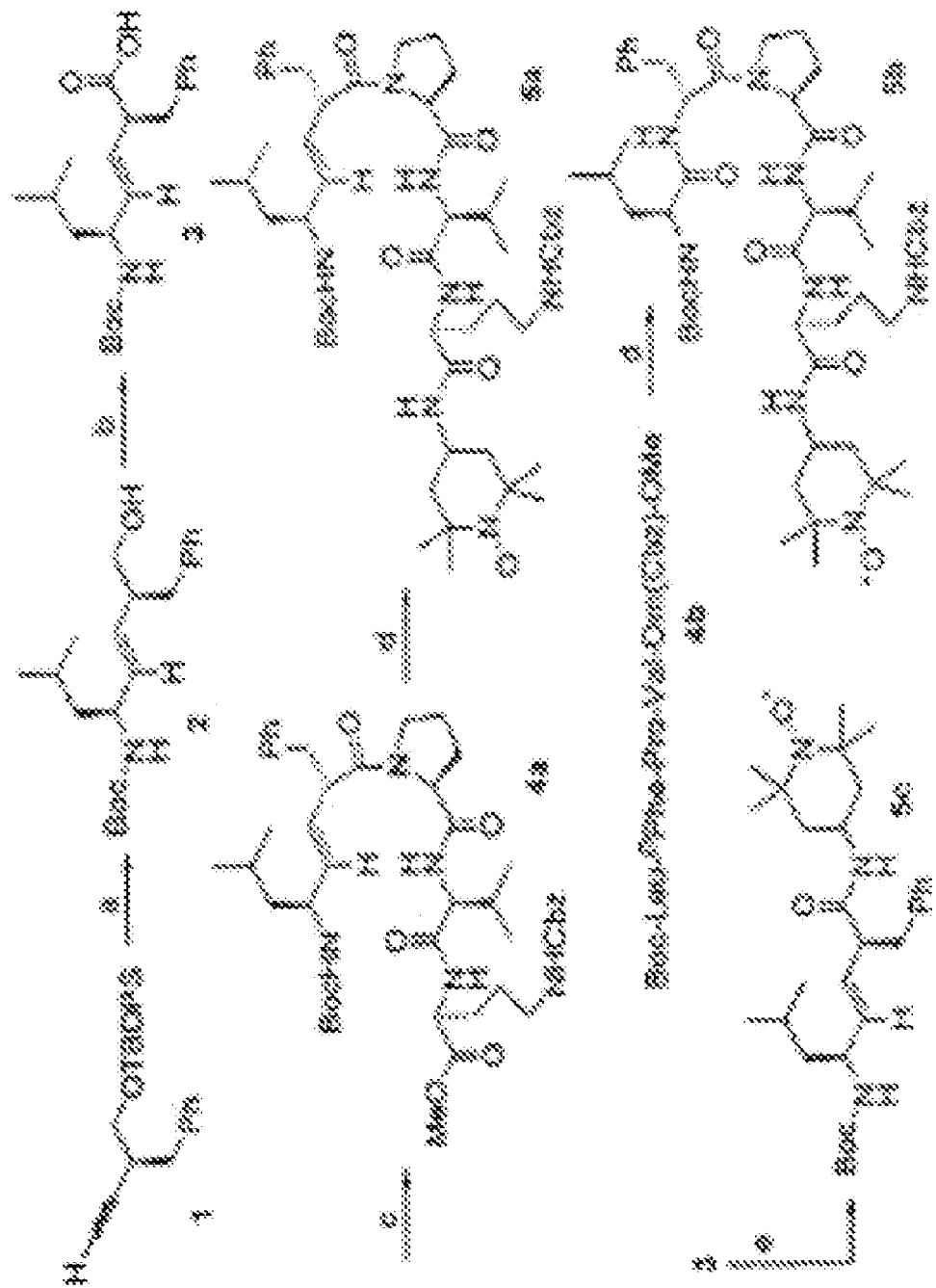
FIG. 2 depicts an example of a synthetic pathway for the TEMPO-hemigramicidin conjugates.

The (E)-alkene, depicted as compound 2 of FIG. 2, was then oxidized in a multi-step process to yield the compound 3 (FIG. 2)—an example of the (E)-alkene isostere.

Then, the compound 3 of FIG. 2 was then conjugated with the peptide H-Pro-Val-Orn(Cbz)-OMe using 1-ethyl-3-(3-dimethylaminopropyl carbodimide hydrochloride) (EDC) as a coupling agent. The peptide is an example of a suitable targeting sequence having affinity for the mitochondria of a cell. The resulting product is shown as compound 4a in FIG. 2. Saponification of compound 4a followed by coupling with 4-amino-TEMPO (4-AT) afforded the resulting conjugate shown as compound 5a in FIG. 2, in which the Leu-$^D$Phe peptide bond has been replaced with an (E)-alkene.

In an alternate embodiment, conjugates 5b and 5c in FIG. 2 were prepared by coupling the peptide 4b (Boc-LeU-$^D$Phe-Pro-Val-Orn(Cbz)-OMe) and the (E)-alkene isostere as indicated as compound 3 in FIG. 2. The peptide is another example of a suitable targeting sequence having an affinity with the mitochondria of a cell.

As is known to one ordinarily skilled in the art, nitroxide and nitroxide derivatives, including TEMPOL and associated TEMPO derivatives are stable radicals that can withstand biological environments. Therefore, the presence of the 4-TEMPO or the TEMPOL "payload" within the mitochondrial membrane can serve as an effective and efficient electron scavenger of the ROS being produced within the membrane.

EXAMPLES

Materials and Methods

Materials. All chemicals were from Sigma-Aldrich (St Louis, Mo.) unless otherwise noted. Heparin, ketamine HCl and sodium pentobarbital were from Abbott Laboratories (North Chicago, Ill.). Dulbecco's modified Eagle medium (DMEM) was from BioWhittaker (Walkersville, Md.). Fetal bovine serum (FBS; <0.05 endotoxin units/ml) was from Hyclone (Logan, Utah). Pyrogen-free sterile normal saline solution was from Baxter (Deerfield, Ill.).

General. All moisture-sensitive reactions were performed using syringe-septum cap techniques under an $N_2$ atmosphere and all glassware was dried in an oven at 150° C. for 2 h prior to use. Reactions carried out at −78° C. employed a $CO_2$-acetone bath. Tetrahydrofuran (THF) was distilled over sodium/benzophenone ketyl; $CH_2Cl_2$, toluene and $Et_3N$ were distilled from $CaH_2$.$Me_2Zn$ was purchased from Aldrich Company.

Reactions were monitored by thin layer chromatography (TLC) analysis (EM Science pre-coated silica gel 60 $F_{254}$ plates, 250 μm layer thickness) and visualization was accomplished with a 254 nm UV light and by staining with a Vaughn's reagent (4.8 g $(NH_4)_6Mo_7O_{24}.4H_2O$, 0.2 g $Ce(SO_4)_2.4H_2O$ in 10 mL conc. $H_2SO_4$ and 90 mL H chromatography on $SiO_2$ was used to purify the crude reaction mixtures.

Melting points were determined using a Laboratory Devices Mel-Temp II. Infrared spectra were determined on a Nicolet Avatar 360 FT-IR spectrometer. Mass spectra were obtained on a Waters Autospec double focusing mass spectrometer (EI) or a Waters Q-Tof mass spectrometer (ESI). LC-MS data were obtained on an Agilent 1100 instrument, using a Waters Xterra MS $C_{18}$ 3.5 μm RP column (4.6×100 mm).

Synthesis, Example I. Prepared as a colorless oil (FIG. 2, compound 1) according to the literature procedure, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf, P. et al., *Convergent Approach to (E)-Alkene and Cyclopropane Peptide Isosteres* J. ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005).

A solution of 2.20 g (5.52 mmol) of compound 1 (FIG. 2) in 20.0 mL of dry $CH_2Cl_2$ was treated at room temperature with 1.85 g (7.17 mmol) of $Cp_2ZrHCl$. The reaction mixture was stirred at room temperature for 5 min, $CH_2Cl_2$ was removed in vacuo and 20.0 mL of toluene was added. The resulting yellow solution was cooled to −78° C. and treated over a period of 30 min with 2.76 mL (5.52 mmol) of $Me_2Zn$ (2.0 M solution in toluene). The solution was stirred at −78° C. for 30 min, warmed to 0° C. over a period of 5 min and treated in one portion with 2.05 g (11.1 mmol) of N-Boc-isovaleraldimine, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane*

Peptide Isosteres J. ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005).

The resulting mixture was stirred at 0° C. for 2 h, quenched with saturated $NH_4Cl$, diluted with EtOAc, filtered through a thin pad of Celite, and extracted with EtOAc. The organic layer was dried ($MgSO_4$), concentrated in vacuo, and purified by chromatography on $SiO_2$ (20:1, hexane/EtOAc) to yield 3.13 g (97%) as a colorless, oily 1:1 mixture of diastereomers.

A solution of 4.19 g (7.15 mmol) of product in 100 mL of dry tetrahydrofuran (THF) was treated at 0° C. with 9.30 mL (9.30 mmol) of Tetrabutylammoniumflouride (TBAF, 1.0 M solution in THF). The reaction mixture was stirred at room temperature for 20 h, diluted with EtOAc, and washed with brine. The organic layer was dried ($MgSO_4$), concentrated in vacuo, and purified by chromatography on $SiO_2$ (4:1, hexane/EtOAc) to yield 1.89 g (76%) as a light yellowish, foamy 1:1 mixture of diastereomers.

A solution of 1.86 g (5.23 mmol) of product in 40.0 mL of dry $CH_2Cl_2$ was treated at 0° C. with 1.46 mL (10.5 mmol) of triethylamine (TEA), 2.02 mL (21.4 mmol) of $Ac_2O$, and 63.9 mg (0.523 mmol) of 4-(dimethylamino) pyridine (DMAP). The reaction mixture was stirred at 0° C. for 15 min and at room temperature for 3 h, diluted with EtOAc, and washed with brine. The organic layer was dried ($MgSO_4$), concentrated in vacuo, and purified by chromatography on $SiO_2$ (20:1, hexane/$Et_2O$) to yield 1.97 g (94%) of acetic acid (2S)-benzyl-(5R)-tert-butoxycarbonylamino-7-methyloct-(3E)-enyl ester (807 mg, 38.7%), acetic acid (2S)-benzyl-(5S)-tert-butoxycarbonylamino-7-methyloct-(3E)-enyl ester (826 mg, 39.6%), and a mixture of the aforementioned species (337 mg, 16.2%).

A solution of 350 mg (0.899 mmol) of acetic acid (2S)-benzyl-(5S)-tert-butoxycarbonylamino-7-methyloct-(3E)-enyl ester in 8.00 mL of MeOH was treated at 0° C. with 62.0 mg (0.449 mmol) of $K_2CO_3$. The reaction mixture was stirred at 0° C. for 1 h and at room temperature for an additional 4 h, diluted with EtOAc, and ashed with $H_2O$. The organic layer was dried ($MgSO_4$), concentrated in vacuo, and purified by chromatography on $SiO_2$ (4:1, hexane/EtOAc) to yield 312 mg (quant.) of compound 2 (FIG. 2) as a colorless oil.

A solution of 23.0 mg (66.2 µmol) of compound 2 (FIG. 2) in 2.00 mL of dry $CH_2Cl_2$ was treated at 0° C. with 42.1 mg (99.3 µmol) of Dess-Martin Periodinane. The reaction mixture was stirred at 0° C. for 1 h and at room temperature for an additional 4 h, quenched with saturated $Na_2S_2O_3$ in a saturated $NaHCO_3$ solution, stirred for 30 min at room temperature, and extracted with $CH_2Cl_2$. The organic layer was dried ($Na_2SO_4$), concentrated in vacuo to give a colorless foam and subsequently dissolved in 3.00 mL of THF, and treated at 0° C. with 300 µL (600 µmol) of 2-methyl-2-butene (2.0 M solution in THF) followed by another solution of 18.0 mg (199 µmol) of $NaClO_2$ and 18.2 mg (132 µmol) of $NaH_2PO_4.H_2O$ in 3.00 mL of $H_2O$. The reaction mixture was stirred at 0° C. for 1 h and at room temperature for an additional 3 h, extracted with EtOAc, and washed with $H_2O$. The organic layer was dried ($Na_2SO_4$) and concentrated in vacuo to yield compound 3 (FIG. 2) as a crude colorless foam that was used for the next step without purification.

A solution of crude compound 3 (FIG. 2) (66.2 µmol) in 3.00 mL of $CHCl_3$ was treated at 0° C. with 10.7 mg (79.2 µmol) of HOBt and 14.0 mg (73.0 µmol) of ethylene dichloride (EDC), followed by a solution of 62.9 mg (132 µmol) of H-Pro-Val-Orn(Cbz)-OMe, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf, P. et al., *Convergent Approach to (E)-Alkene and Cyclopropane Peptide Isosteres* J. ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005), in 1.00 mL of $CHCl_3$ and 0.8 mg (6.6 µmol) of DMAP. The reaction mixture was stirred at room temperature for 2 d, diluted with $CHCl_3$, and washed with $H_2O$. The organic layer was dried ($Na_2SO_4$), concentrated in vacuo, and purified by chromatography on $SiO_2$ (from 2:1, hexane/EtOAc to 20:1, $CHCl_3$/MeOH) to yield 51.3 mg (94%) of compound 4a (FIG. 2) as a colorless foam.

A solution of 53.7 mg (65.5 µmol) of compound 4a (FIG. 2) in 2.00 mL of MeOH was treated at 0° C. with 655 µL (655 µmol) of 1 N NaOH. The reaction mixture was stirred at room temperature for 6 h, and treated with 655 µL (655 µmol) of 1 N HCl. The solution was extracted with $CHCl_3$ and the organic layer was dried ($Na_2SO_4$) and concentrated in vacuo to give the crude acid as a colorless form. This acid was dissolved in 5.00 mL of $CHCl_3$ and treated at room temperature with 10.6 mg (78.4 µmol) of HOBt, 15.1 mg (78.8 µmol) of EDC, 20.2 mg (118 µmol) of 4-amino-TEMPO and 8.0 mg (65.5 µmol) of DMAP. The reaction mixture was stirred at room temperature for 36 h, diluted with $CHCl_3$, and washed with $H_2O$. The organic layer was dried ($Na_2SO_4$), concentrated in vacuo, and purified by chromatography on $SiO_2$ (from 1:1, hexane/EtOAc to 20:1, $CHCl_3$/MeOH) to yield 62.0 mg (99%) of compound 5a (FIG. 2) as a colorless solid. The following characterization data were obtained: LC-MS (Rt 8.81 min, linear gradient 70% to 95% $CH_3CN$ ($H_2O$) in 10 min, 0.4 mL/min; m/z=959.5 $[M+H]^+$, 981.5 $[M+Na]^+$) and HRMS (ESI) m/z calculated for $C_{53}H_{80}N_7O_9Na$ (M+Na) 981.5915, found 981.5956.

A solution of 60.0 mg (71.7 µmol) of compound 4b (FIG. 2), see Tamaki, M. et al. I. BULL. CHEM. SOC. JPN. 66:3113 (1993), in 2.15 mL of MeOH was treated at room temperature with 717 µL (717 µmol) of 1 N NaOH. The reaction mixture was stirred at room temperature for 5 h, and treated at 0° C. with 717 µL (717 µmol) of 1 N HCl. The solution was extracted with $CHCl_3$ and the organic layer was dried ($Na_2SO_4$) and concentrated in vacuo to give the crude acid as colorless foam. The acid was dissolved in 6.04 mL of $CHCl_3$ and treated at room temperature with 11.6 mg (85.8 µmol) of HOBt, 16.5 mg (85.1 µmol) of EDC, 18.5 mg (108 µmol) of 4-amino-TEMPO and 8.8 mg (72.0 µmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 2:1, hexane/EtOAc; to 20:1, $CHCl_3$/MeOH) to yield 69.6 mg (99%) of compound 5b (FIG. 2) as a yellowish solid. The following characterization data were obtained: LC-MS (Rt 7.02 min, linear gradient 70% to 95% $CH_3CN$ ($H_2O$) in 10 min, 0.4 mL/min; m/z=976.5 $[M+H]^+$, 998.4 $[M+Na]^+$) and HRMS (ESI) m/z calculated for $C_{52}H_{79}N_8O_{10}Na$ (M+Na) 998.5817, found 998.5774.

A solution of crude compound 3 (FIG. 2) (40.3 µmol) in 3.00 mL of $CH_2Cl_2$ was treated at 0° C. with 10.4 mg (60.7 µmol) of 4-amino-TEMPO, 7.7 mg (40.2 µmol) of EDC, and 5.4 mg (44.2 µmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 4:1 to 1:1, hexane/EtOAc) to yield 18.8 mg (91%) of compound 5c (FIG. 2) as a yellowish solid. The following characterization data were obtained: LC-MS ($R_t$ 7.01 min, linear gradient 70% to 95% $CH_3CN$ ($H_2O$) in 10 min, 0.4 mL/min; m/z=537.3 [M+Na]$^+$) and HRMS (ESI) m/z calculated for $C_{30}H_{48}N_3O_4Na$ (M+Na) 537.3543, found 537.3509.

Determination of intracellular superoxide radicals Oxidation-dependent fluorogenic dye, dihydroethidium (DHE, Molecular Probes) was used to evaluate intracellular production of superoxide radicals. DHE is cell permeable and, in the presence of superoxide, is oxidized to fluorescent ethidium which intercalates into DNA. The fluorescence of ethidium was measured using a FACscan (Becton-Dickinson, Rutherford, N.J.) flow cytometer, equipped with a 488-nm argon ion laser and supplied with the Cell Quest software. Mean fluorescence intensity from 10,000 cells were acquired using a 585-nm bandpass filter (FL-2 channel).

Determination of intracellular ATP levels. Cells were incubated with 10 μm of compound 5a (FIG. 2) for indicated periods of time (2, 4, 6, 12, and 14 h). At the end of incubation, cells were collected and the content of intracellular ATP was determined using a bioluminescent somatic cell assay kit (Sigma, St. Louis, Mass.). As a positive control, cells were incubated with 2 mM of 2-dexy-glucose, a glucose analogue which competitively inhibits cellular uptake and utilization of glucose, for 12 and 14 h.

Cells. Caco-$2_{BBe}$ human enterocyte-like epithelial cells were obtained from the American Type Culture Collection (Manassas, Va.). Cells were routinely maintained at 37° C. in under a humidified atmosphere containing 8% $CO_2$ in air. The culture medium was DMEM supplemented with 10% FBS, non-essential amino acids supplement (Sigma-Aldrich catalogue #M7145), sodium pyruvate (2 mM), streptomycin (0.1 mg/ml), penicillin G (100 U/ml) and human transferrin (0.01 mg/ml). The culture medium was changed 3 times per week.

Surgical procedures to obtain vascular access. All study protocols using rats followed the guidelines for the use of experimental animals of the US National Institutes of Health and were approved by the Institutional Animal Care and Use Committee at the University of Pittsburgh.

Male specific pathogen-free Sprague Dawley rats (Charles River Laboratories, Wilmington, Mass.), weighing 150-250 g, were housed in a temperature-controlled environment with a 12-h light/dark cycle. The rats had free access to food and water. For experiments, rats were anesthetized with intramuscular ketamine HCl (30 mg/kg) and intraperitoneal sodium pentobarbital (35 mg/kg). Animals were kept in a supine position during the experiments. Lidocaine (0.5 ml of a 0.5% solution) was injected subcutaneously to provide local anesthesia at surgical cut-down sites. In order to secure the airway, a tracheotomy was performed and polyethylene tubing (PE 240; Becton Dickinson, Sparks, Md.) was introduced into the trachea. Animals were allowed to breathe spontaneously.

The right femoral artery was cannulated with polyethylene tubing (PE 10). This catheter was attached to a pressure transducer that allowed instantaneous measurement of mean arterial pressure (MAP) during the experiment. For experiments using the pressure-controlled hemorrhagic shock (HS) model, the right jugular vein was exposed, ligated distally, and cannulated with polyethylene tubing (PE 10) in order to withdraw blood. For experiments using the volume-controlled hemorrhagic shock (HS) model, the jugular catheter was used to infuse the resuscitation solution and the right femoral vein, which was cannulated with a silicon catheter (Chronic-Cath, Norfolk Medical, Skokie, Ill.), was used to withdraw blood.

All animals were instrumented within 30 min. Heparin (500 U/kg) was administered immediately after instrumentation through the femoral vein. Animals were placed in a thermal blanket to maintain their body temperature at 37° C. The positioning of the different devices aforementioned was checked postmortem.

Intestinal mucosal permeability assay. Animals were allowed access to water but not food for 24 h prior to the experiment in order to decrease the volume of intestinal contents. The rats were instrumented as described above.

A midline laparotomy was performed and the small intestine was exteriorized from the duodenojejunal junction to the ileocecal valve. A small incision was made on the antimesenteric aspect of the proximal small intestine and saline solution (1.5 ml) was injected. The bowel was ligated proximally and distally to the incision with 4-0 silk (Look, Reading, Pa.).

The small intestine was compressed gently in aboral direction along its length to displace intestinal contents into the colon. Starting 5 cm from the ileocecal valve, the ileum was partitioned into six contiguous water-tight segments. Each segment was 3 cm long and was bounded proximally and distally by constricting circumferential 4-0 silk sutures. Care was taken to ensure that the vascular supply to intestine was not compromised, and each segment was well-perfused.

Two randomly selected segments in each rat were injected with 0.3 ml of vehicle and served as "no treatment" controls. In order to fill the segments, a small incision was made and the solution was injected using a Teflon catheter (Abbocath 16Ga, Abbot Laboratories).

The remaining four other segments were injected with solutions containing either 4-hydroxy-2,2,6,6-tetramethylpiperidine-N-oxyl (TEMPOL) or one of the gramicidin S-based compounds. Four different final concentrations of TEMPOL in normal saline were evaluated: 0.1, 1, 5 and 20 mM. The hemigramicidin-based compounds were dissolved in a mixture of dimethylsulfoxide (DMSO) and normal saline (1:99 v/v) and injected at final concentrations of 0.1, 1, 10 or 100 M. After the segments were loaded with saline or the test compounds, the bowel was replaced inside the peritoneal cavity and the abdominal incision was temporarily closed using Backhaus forceps.

After a 5 min stabilization period, hemorrhagic shock was induced by withdrawing blood via the jugular catheter. MAP was maintained at 30±3 mm Hg for 2 hours. The shed blood was re-infused as needed to maintain MAP within the desired range.

After 2 h of shock, the animals were euthanized with an intracardiac KCl bolus injection. The ileum was rapidly excised from the ileocecal valve to the most proximal gut segment. The tips of each segment were discarded. In order to assay caspases 3 and 7 activity and phospholipids peroxidation, mucosa samples were collected from gut segments immediately after hemorrhage and stored at −80° C. For permeability measurements, each segment was converted into an everted gut sac, as previously described by Wattanasirichaigoon et al., see Wattanasirichaigoon, S. et al., *Effect of mesenteric ischemia and reperfusion or hemorrhagic shock on intestinal mucosal permeability and ATP content in rats*, Shock, 12:127-133 (1999).

Briefly, as per the Wattanasirichaigoon protocol referenced above, the sacs were prepared in ice-cold modified Krebs-Henseleit bicarbonate buffer (KHBB, pH 7.4). One end of the gut segment was ligated with a 4-0 silk suture; the segment was then everted onto a thin plastic rod. The resulting gut sac was mounted on a Teflon catheter (Abbocath 16GA, Abbot Laboratories) connected to a 3 ml plastic syringe containing 1.5 ml of Krebs Henseleit bicarbonate buffer (KHBB). The sac was suspended in a beaker containing KHBB plus fluorescein-isothiocyanate labeled dextran (average molecular mass 4 kDa; FD4; 0.1 mg/ml). This solution was maintained at 37° C., and oxygenated by bubbling with a gas mixture ($O_2$ 95%/$CO_2$ 5%). After 30 min, the fluid within the gut sac was collected. The samples were cleared by centrifugation at 2000 g for 5 min.

Fluorescence of FD4 in the solution inside the beaker and within each gut sac was measured using a fluorescence spectrophotometer (LS-50, Perkin-Elmer, Palo Alto, Calif.) at an excitation wavelength of 492 nm and an emission wavelength of 515 nm. Mucosal permeability was expressed as a clearance normalized by the length of the gut sac with units of $nL \cdot min^{-1} \cdot cm^{-1}$, as previously described, see Yang, R. et al., *Ethyl pyruvate modulates inflammatory gene expression in mice subjected to hemorrhagic shock*, AM. J. PHYSIOL. GASTROINTEST. LIVER PHYSIOL. 283:G212-G22 (2002).

Results for a specific experimental condition (i.e., specific test compound at a single concentration) were expressed as relative change in permeability calculated according to this equation: Relative change in permeability (%)=$(C_{HS\,exp} - C_{normal})/C_{HS\,cont} - C_{normal}) \times 100$, where $C_{HS\,exp}$ is the clearance of FD4 measured for a gut segment loaded with the experimental compound, $C_{normal}$ is the clearance of FD4 measured in 6 gut segments from 3 normal animals not subjected to hemorrhagic shock, and $C_{HS\,cont}$ is the mean clearance of FD4 measured in 2 gut segments filled with vehicle from the same animal used to measure $C_{HS\,exp}$.

Measurement of permeability of Caco-2 $_{BBe}$ monolayers. Caco-2 $_{BBe}$ cells were plated at a density of $5 \times 10^{-4}$ cells/well on permeable filters (0.4 µm pore size) in 12-well bicameral chambers (Transwell, Costar, Corning, N.Y.). After 21 to 24 days, paracellular permeability was determined by measuring the apical-to-basolateral clearance of FD4.

Briefly, the medium on the basolateral side was replaced with control medium or medium containing menadione (50 µM final). Medium containing FD4 (25 mg/ml) was applied to the apical chamber. In some cases, one of the gramicidin S-based compounds, XJB-5-131, also was added to the apical side at final concentrations of 0.1, 1, 10 or 100 µM. After 6 hours of incubation, the medium was aspirated from both compartments. Permeability of the monolayers was expressed as a clearance ($pL \cdot h^{-1} \cdot cm^{-2}$), see Han, X. et al., *Proinflammatory cytokines cause $NO^{\bullet-}$ dependent and independent changes in expression and localization of tight junction proteins in intestinal epithelial cells*, SHOCK 19:229-237 (2003).

Caspases 3 and 7 activity assay. Caspases 3 and 7 activity was measured using a commercially available assay kit, Caspase Glo™ 3/7 assay kit (Promega, Madison, Wis.). Briefly, 50 µl of rat gut mucosa homogenate (20 µg protein) was mixed with 50 µl of Caspase-Glo™ reagent and incubated at room temperature for 1 hour. At the end of incubation period, the luminescence of each sample was measured using a plate reading chemiluminometer (ML1000, Dynatech Laboratories, Horsham, Pa.). Activity of caspases 3 and 7 was expressed as luminescence intensity (arbitrary units per mg protein). Protein concentrations were determined using the BioRad assay (Bio-Rad Laboratories, Inc., Hercules, Calif.).

Assay for peroxidation of phospholigids. Gut mucosal samples were homogenized. Lipids were extracted from homogenates using the Folch procedure, see Folch, J., M. Lees, and G. H. Sloan-Stanley, *A simple method for isolation and purification of total lipids from animal tissue*, J. BIOL. CHEM. 226:497-509 (1957), and resolved by 2D HPTLC (High Performance Thin Layer Chromatography) as previously described, see Kagan, V. E. et al., *A role for oxidative stress in apoptosis: Oxidation and externalization of phosphatidylserine is required for macrophage clearance of cell undergoing Fas-mediated apoptosis*, J. IMMUNOL. 169:487-489 (2002). Spots of phospholipids were scraped from HPTLC plates and phospholipids were extracted from silica. Lipid phosphorus was determined by a micro-method, see Bottcher, C. J. F. et al., *A rapid and sensitive sub-micro phosphorus determination*, ANAL. CHIM. ACTA 24: 203-204 (1961).

Oxidized phospholipids were hydrolyzed by pancreatic phospholipase $A_2$ (2 U/µl) in 25 mM phosphate buffer containing 1 mM $CaCl_2$, 0.5 mM EDTA and 0.5 mM sodium dodecyl sulfate (SDS) (pH 8.0, at room temperature for 30 min). Fatty acid hydroperoxides formed were determined by fluorescence HPLC of resorufin stoichiometrically formed during their microperoxidase 11-catalyzed reduction in presence of Amplex Red (for 40 min at 4° C.) (8). Fluorescence HPLC (Eclipse XDB-C18 column, 5 µm, 150×4.6 mm, mobile phase was composed of 25 mM disodium phosphate buffer (pH 7.0)/methanol (60:40 v/v); excitation wavelength 560 nm, emission wavelength 590 nm) was performed on a Shimadzu LC-100AT HPLC system equipped with fluorescence detector (RF-10Axl) and autosampler (SIL-10AD).

Survival of rats subjected to volume-controlled hemorrhagic shock. Following surgical preparation and a 5-min stabilization period to obtain baseline readings, rats were subjected to hemorrhagic shock. Bleeding was carried out in 2 phases.

Initially, 21 ml/kg of blood was withdrawn over 20 min. Immediately thereafter, an additional 12.5 ml/kg of blood was withdrawn over 40 min. Thus, hemorrhage occurred over a total period of 60 min and the total blood loss was 33.5 ml/kg or approximately 55% of the total blood volume. Rats were randomly assigned to receive XJB-5-131 (2 µmol/kg) or its vehicle, a 33:67 (v/v) mixture of DMSO and normal saline. XJB-5-131 solution or vehicle alone was administered as a continuous infusion during the last 20 min of the hemorrhage period. The total volume of fluid infused was 2.8 ml/kg and it was administered intravenously using a syringe pump (KD100, KD Scientific, New Hope, Pa.). Rats were observed for 6 hours or until expiration (defined by apnea for >1 min). At the end of the 6 hour observation period, animals that were still alive were euthanized with an overdose of KCl.

Blood pressure was recorded continuously using a commercial strain-gauge transducer, amplifier, and monitor (S90603a, SpaceLabs, Redmond, Wash.). Blood samples (0.5 ml) were collected from the jugular vein at the beginning of hemorrhage (baseline), at the end of hemorrhage (shock) and at the end of resuscitation (resuscitation). Hemoglobin concentration [Hb], lactate and glucose concentration were determined using an auto-analyzer (Model ABL 725, Radiometer Copenhagen, Westlake, Ohio).

Data presentation and statistics. All variables are presented as means±Standard Error Mean (SEM). Statistical significance of differences among groups was determined using ANOVA (analysis of variance) and LSD (Least Significant Difference) tests, or Kruskal-Wallis and Mann-Whitney tests as appropriate. Survival data were analyzed using the log-rank test. Significance was declared for p values less than 0.05.

EXAMPLE I

Selective delivery of TEMPO to mitochondria could lead to therapeutically beneficial reduction of ROS; therefore, investigation of the use of conjugates of 4-amino-TEMPO (4-AT) was explored. In order to selective target the mitochondria, a targeting sequence using the membrane active antibiotic Gramicidin S (GS) as well as corresponding alkene isosteres, shown in FIGS. 1 and 2. Accordingly, using the Gramicidin S peptidyl fragments and alkene isosteres as "anchors," the TEMPO "payload" could be guided into the mitochondria.

The Leu-$^D$Phe-Pro-Val-Orn fragment of hemigramicidin was used as a targeting sequence. Alkene isosteres such as (E)-alkene isosteres of Gramicidin S (i.e., hemigramicidin) were used as part of the targeting sequence. See FIG. 3 for the synthetic pathway for (E)-alkene isosteres and compound 3 for the corresponding chemical structure. The (E)-alkene as depicted in compound 2 of FIG. 2 was then oxidized in a multi-step process to yield the compound as depicted in compound 3—an example of the (E)-alkene isostere.

Then, the compound depicted as compound 3 of FIG. 2 was then conjugated with the tripeptide H-Pro-Val-Orn(Cbz)-OMe using EDC (1-ethyl-3-(3-dimethylaminopropyl) carbodiimide hydrochloride) as a coupling agent. The tripeptide is an example of a suitable targeting sequence having affinity for the mitochondria of a cell. The resulting product is shown as compound 4a in FIG. 2. Saponification of compound 4a followed by coupling with 4-amino-TEMPO (4-AT) afforded the resulting conjugate shown as compound 5a in FIG. 2, in which the Leu-$^D$Phe peptide bond has been replaced with an (E)-alkene.

Figure 3:
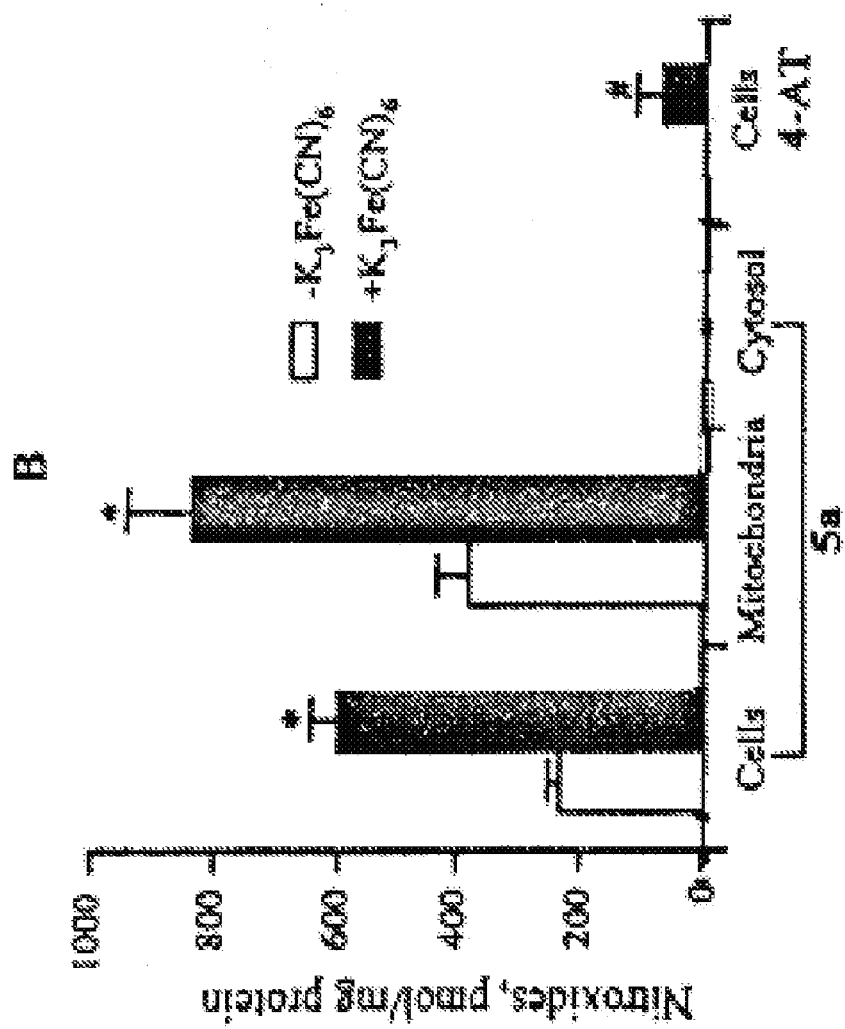
FIG. 3 shows an EPR-based analysis of integration and reduction of nitroxide Gramicidin S peptidyl-TEMPO conjugates in MECs.
Figure 3:
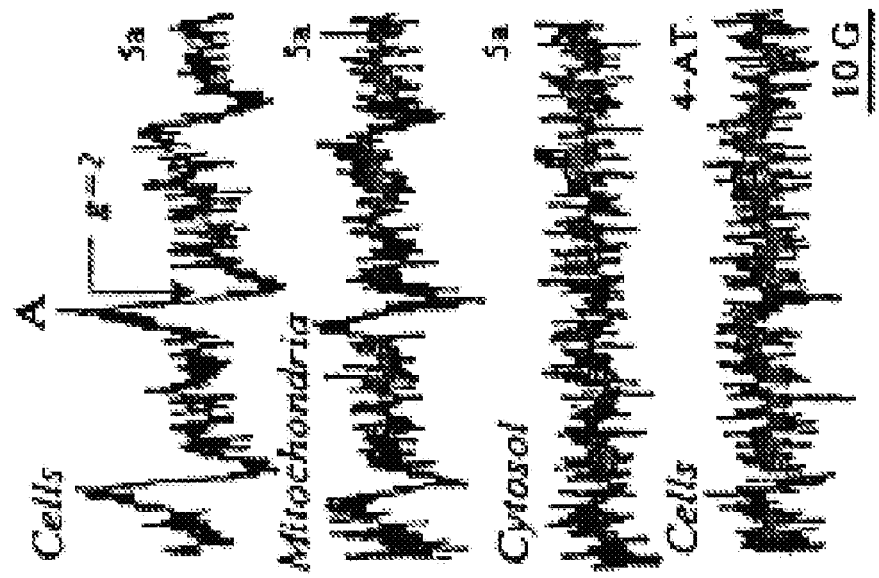
Figure 4:
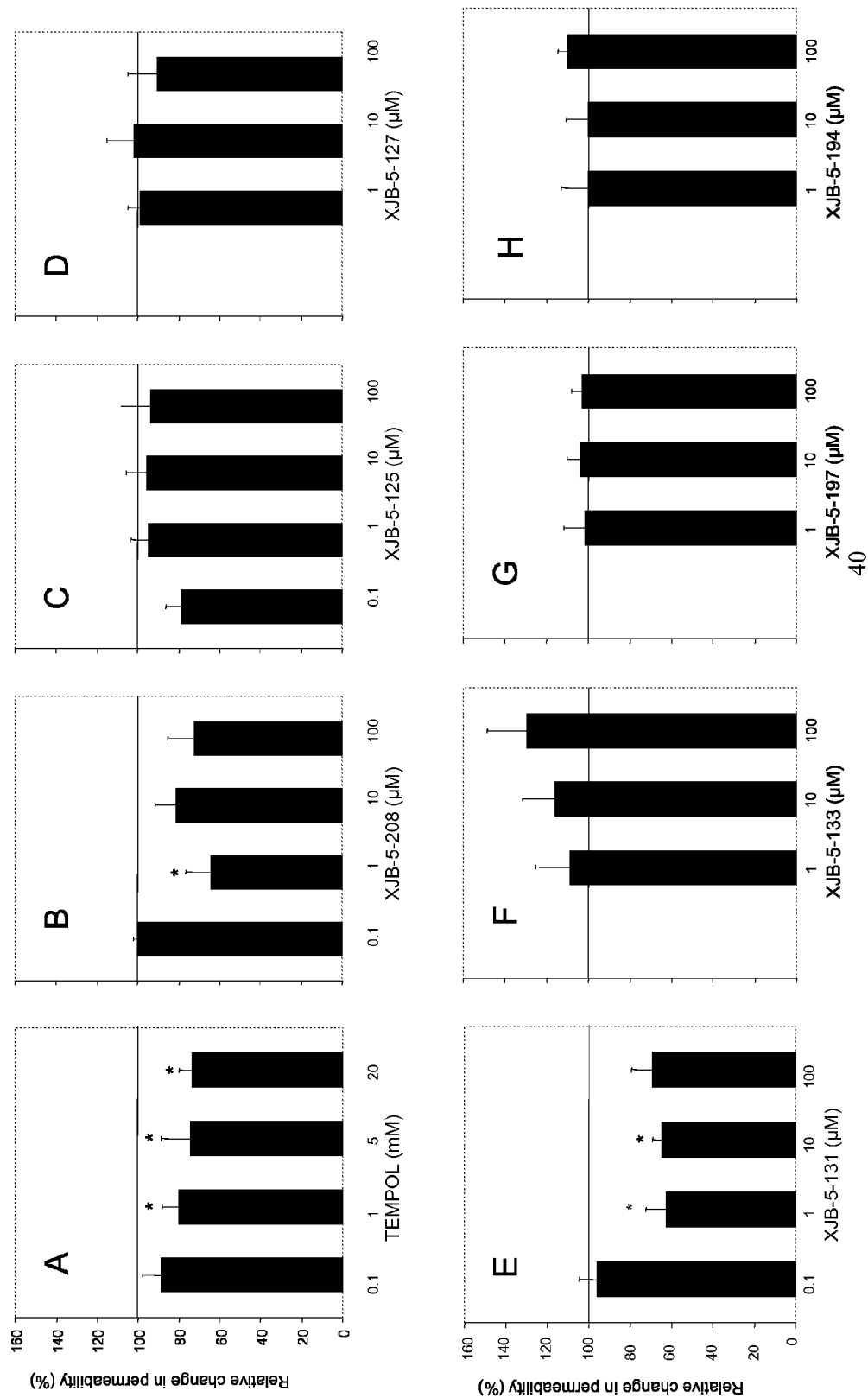
FIG. 4 shows an flourescein isothiocyanate-dextran (FD4) read-out which reflects the effect of Gramicidin-S TEMPO conjugates on rat ileal mucosal permeability following profound hemorrhagic shock. Data are expressed as a percentage of the change permeability relative to that observed in simultaneously assayed control segments loaded during shock with normal saline solution.

In an alternate embodiment, conjugates 5b and 5c in FIG. 2 by coupling the peptide 4b (Boc-Leu-$^D$Phe-Pro-Val-Orn (Cbz)-OMe) and the (E)-alkene isostere as indicated as compound 3 in FIG. 2 to 4-AT. The peptide is another example of a suitable targeting sequence having an affinity with the mitochondria of a cell.

Electron paramagnetic resonance ("EPR") spectroscopy was used to monitor the cellular delivery of compounds 5a and 5b shown in FIG. 2 in mouse embryonic cells ("MEC").

The following conditions were used during the EPR-based analysis of the integration and reduction of nitroxide Gramicidin S-peptidyl conjugates in MECs. The MECs at a concentration of 10 million MECs per mL were incubated with 10 μM of 4-amino-TEMPO (4-AT) and 5a, respectively. Recovered nitroxide radicals in whole cells, mitochondria, and cytosol fractions were resuspended in phosphate buffer saline (PBS) in the presence and absence, respectively, of 2 mM $K_3Fe(CN)_6$. In brief, FIG. 3A shows a representative EPR spectra of 5a in different fractions of MECs in the presence of $K_3Fe(CN)_6$. Further, FIG. 3B shows an assessment of integrated nitroxides.

Distinctive characteristic triplet signals of nitroxide radicals were detected in MECs incubated with 10 μM of compound 5a (FIG. 2) as well as in mitochondria isolated from these cells. The cystolic function did not elicit EPR signals of nitroxide radicals; similar results were observed with conjugate 5b (FIG. 2) (data not shown).

Incubation of MECs with 5a (FIG. 2) resulted in integration and one-electron reduction of 5a, as evidenced by a significant increase in magnitude of the EPR signal intensity upon addition of a one-electron oxidant, ferricyanide (FIG. 3B). (Note: EPR results for incubation of MECs with 5b are not shown in FIG. 3; however, EPR results for 5b were similar when compared to 5a). In contrast to 5a and 5b, however, 4-amino-TEMPO (4-AT) did not effectively permeate cells or the mitochondria, as shown by the absence of significant amplitude change in the EPR results for 4-AT.

The ability of 5a, 5b (FIG. 2), and 4-AT to prevent intracellular superoxide generation by flow cytometric monitoring of oxidation of dihydroehtidium ("DHE") to a fluorescent ethidium was tested. The ability of 5a, 5b, and 4-AT to protect cells against apoptosis triggered by actinomycin D (ActD) was also tested. MECs pretreated with 10 μM 4-AT, 5a, or 5b then incubated with ActD at a concentration of 100 ng/mL. It was found that 5a and 5b completely inhibited nearly two-fold intracellular superoxide generation in MECs (see FIG. 5A). 4-AT had no effect on the superoxide production in MECs.

Apoptotic cell responses were documented using three biomarkers: (1) externalization of phosphatidylserine (PS) on the cell surface (by flow cytometry using an FITC-labeled PS-binding protein, annexin V, see FIGS. 5B and 5E); (2) activation of caspase-3 by cleavage of the Z-DEVD-AMC substrate (see FIG. 5C), and, (3) DNA fragmentation by flow cytometry of propidiium iodide stained DNA (see FIG. 5D).

Phosphatidylserine is an acidic phospholipid located exclusively on the inner leaflet of the plasma membrane; exposure of PS on the cell surface is characteristic of cell apoptosis. Externalization of PS was analyzed by flow cytometry using an annexin V kit. Cells were harvested by trypsinization at the end of incubation and then stained with annexin V-FITC and propidium iodide (PI). Ten thousand cell events were collected on a FACScan flow cytometer. Cells that annexin V-positive and PI-negative were considered apoptotic.

Activation of capase-3, a cystein protease only activated in the execution phase of apoptosis, was determined using an EnzChek capsase-3 assay kit.

Further, calcium and magnesium dependent nucleases are activated that degrade DNA during apoptosis. These DNA fragments are eluted, stained with propidium iodide and analyzed using flow cytometry. A cell population with decreased DNA content was considered a fraction of apoptotic cells.

Anti-apoptotic effects of 5a and 5b were observed at relatively low concentrations of 10 μM. 5a and 5b (FIG. 3) reduced the number of annexin V-positive cells as shown in FIG. 5B, prevented caspase-3 activation as shown in FIG. 5C, and prevented DNA fragmentation as shown in FIG. 5D. At concentrations in excess of 10 μM, both 5a and 5b were either less protective or exhibited cytotoxicity (FIG. 5E). In contrast, 4-AT afforded no protection.

In contrast, 5c, which does not have a complete targeting moiety, was ineffective in protecting MECs against ActD-induced apoptosis (FIGS. 5B and 5C) at low concentrations. Accordingly, the hemigramicidin peptidyl targeting sequence is essential for anti-apoptotic activity of nitroxide conjugates such as those containing TEMPO.

Finally, the reduction of 5a and 5b could also cause inhibition of mitochondrial oxidative phosphorylation, so the ATP levels of MECs treated with these compounds were tested. As is known to one ordinarily skilled in the art, ATP serves as the primary energy source in biological organisms; reduction of ATP levels would greatly impair normal cell function. ATP levels in MECs in the presence or absence of 5a or 2-deoxyglucose (2-DG) were used as a positive control (see FIG. 5F). At concentrations at which anti-apoptotic effects were maximal (~10 μM, FIG. 5E), nitroxide conjugates did not cause significant changes in the cellular ATP level. Therefore, synthetic GS-peptidyl conjugates migrate into cells and mitochondria where they are reduced without affecting the ability of the mitochondria to produce ATP.

EXAMPLE II

In an in vivo assay, the ileum of rats was divided into a series of well-vascularized components in a manner akin to links of sausage. The lumen of each ileal compartment was filled with a 3 μL aliquot of test solution. Two of the ileal compartments were filled with vehicle alone (i.e., a solution containing at least in part the TEMPO derivative). These two components served as internal controls to account for individualistic variations in the severity of shock or the response of the mucosa to the shock.

Figure 5:
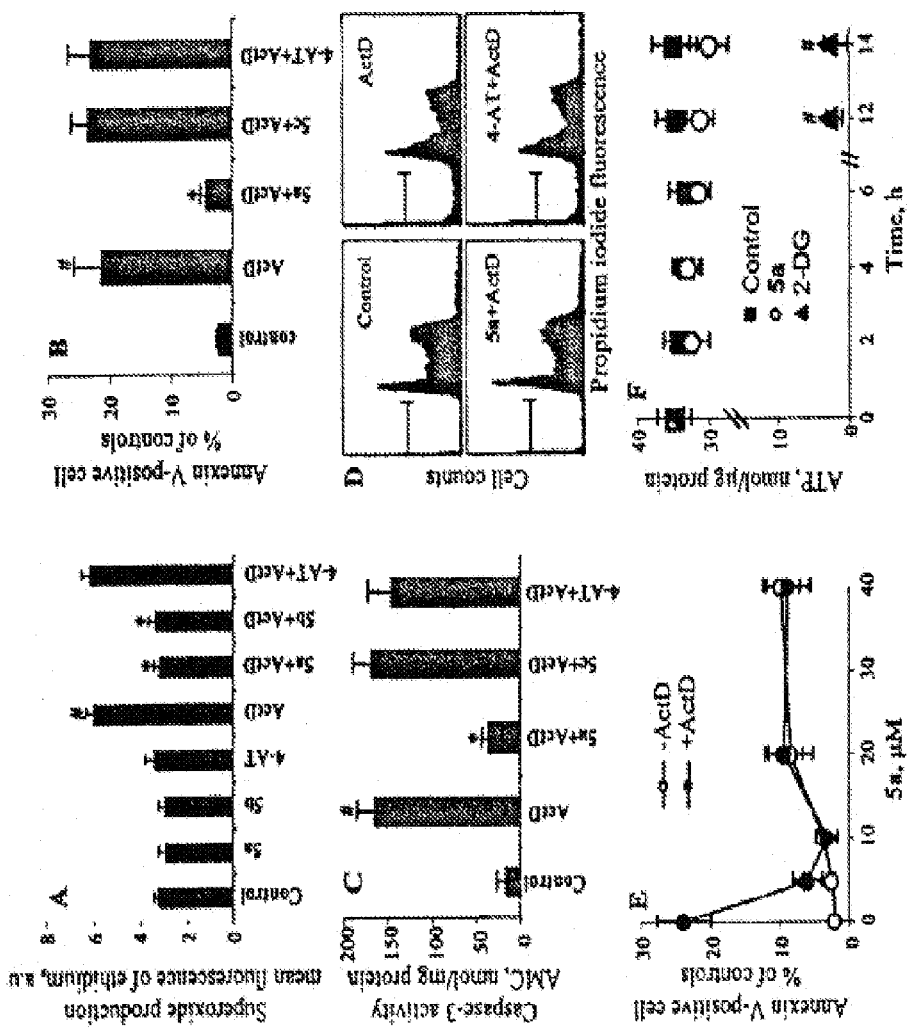
FIG. 5 shows graphical representations of the effect of nitroxide conjugates on ActD-induced apoptosis.

Using this assay system, eight compounds were evaluated as shown in FIG. 5: TEMPOL (FIG. 4A), one dipeptidic TEMPO analog (FIG. 4B—XJB-5-208), 3 hemigramicidin-TEMPO conjugates (FIGS. 4C—XJB-5-125, 4E—XJB-5-131, and 4G—XJB-5-197), and 3 hemigramicidin compounds that do not have the TEMPO moiety (FIGS. 4D—XJB-5-127, 4F—XJB-5-133, and 4H—XJB-5-194).

Hemorrhagic shock in rats leads to marked derangements in intestinal mucosal barrier function—in other words, the mucosal permeability of shocked intestinal segments was significantly greater than the permeability of segments from normal rats ($52.3 \pm 0.5$ versus $6.9 \pm 0.1$ nL·min$^{-1}$·cm$^{-2}$, respectively; $p<0.01$), see Tuominen, E. K. J., C. J. A. Wallace, and P. K. J. Kinnunen, *Phospholipid cytochrome c interaction: evidence for the extended lipid anchorage*, J. BIOL. CHEM., 277:8822-8826 (2002); also Wipf, P. et al., *Mitochondrial targeting of selective electron scavengers: synthesis and biological analysis of hemigramicidin-TEMPO conjugates*, J. AM. CHEM. SOC. 127:12460-12461. Accordingly, mice were subjected to 2 hours of shock (Mean Arterial Pressure ("MAP")=$30 \pm 3$ mm Hg), the gut segments were harvested and mucosal permeability to flourescein isothiocyanate-dextran (FD4) measured ex vivo. Data in FIG. 4 are expressed as a percentage of the change permeability relative to that observed in simultaneously assayed control segments loaded during shock with normal saline solution.

Accordingly, intraluminal TEMPOL was used as a "positive control" for gut mucosal protection assay. TEMPOL concentrations $\geq 1$ mM in the gut lumen ameliorated hemorrhagic shock-induced ileal mucosal hyperpermeability (FIG. 5A). Two of the TEMPO conjugates, namely XJB-5-208 (FIG. 4B) and XJB-5-131 (FIG. 4C), also significantly ameliorated hemorrhagic shock-induced ileal mucosal hyperpermeability. The lowest effective concentration for XJB-5-208 (FIG. 4B) and XJB-5-131 (FIG. 4E) was 1 µM; i.e., both of these compounds were 1000-fold more potent than TEMPOL. Two other compounds carrying the TEMPO payload, XJB-5-125 (FIG. 4C) and XJB-5-197 (FIG. 4G), failed to provide protection against gut barrier dysfunction induced by hemorrhage. XJB-5-133 (FIG. 4F) has the same (hemigramicidin-based) mitochondrial targeting moiety as XJB-5-131 (FIG. 4E) but lacks the TEMPO payload. It is noteworthy, therefore, that XJB-5-133 (FIG. 4F) did not afford protection from the development of ileal mucosal hyperpermeability.

Ineffective as well were the two other hemigramicidin-based compounds that also lacked the TEMPO payload, XJB-5-127 (FIG. 4D) and XJB-5-194 (FIG. 4H). Of the compounds screened, XJB-5-131 (FIG. 4E) appeared to be the most effective, reducing hemorrhagic shock-induced mucosal hyperpermeability to approximately 60% of the control value.

Based upon the results as reflected in FIGS. 4A-4H, both the TEMPO payload and the "anchoring" hemigramicidin fragment are requisite moieties that should be present in order for effective electron scavenging activity by the XJB-5-131 compound. Accordingly, it was found that XJB-5-131 ameliorates peroxidation of mitochondrial phosopholipids (i.e., ROS activity) in gut mucosa from rats subject to hemmorhagic shock.

In the subsequent series of in vivo studies, the affect of intraluminal XJB-5-131 on hemorrhage-induced peroxidation of phospholipids in intestinal mucosa was examined. Isolated segments of the ileum of rats were divided into a series of well-vascularized components in a manner akin to sausage and the lumen of each ileal compartment was filled with the same volume of test solution containing either vehicle or a 10 µM solution of XJB-5-131, which was previously indicated to be the most active of the hemigramicidin-TEMPO conjugates. In a preferred embodiment, 0.3 mL of test solution filled the lumen of each ileal compartment.

Figure 6:
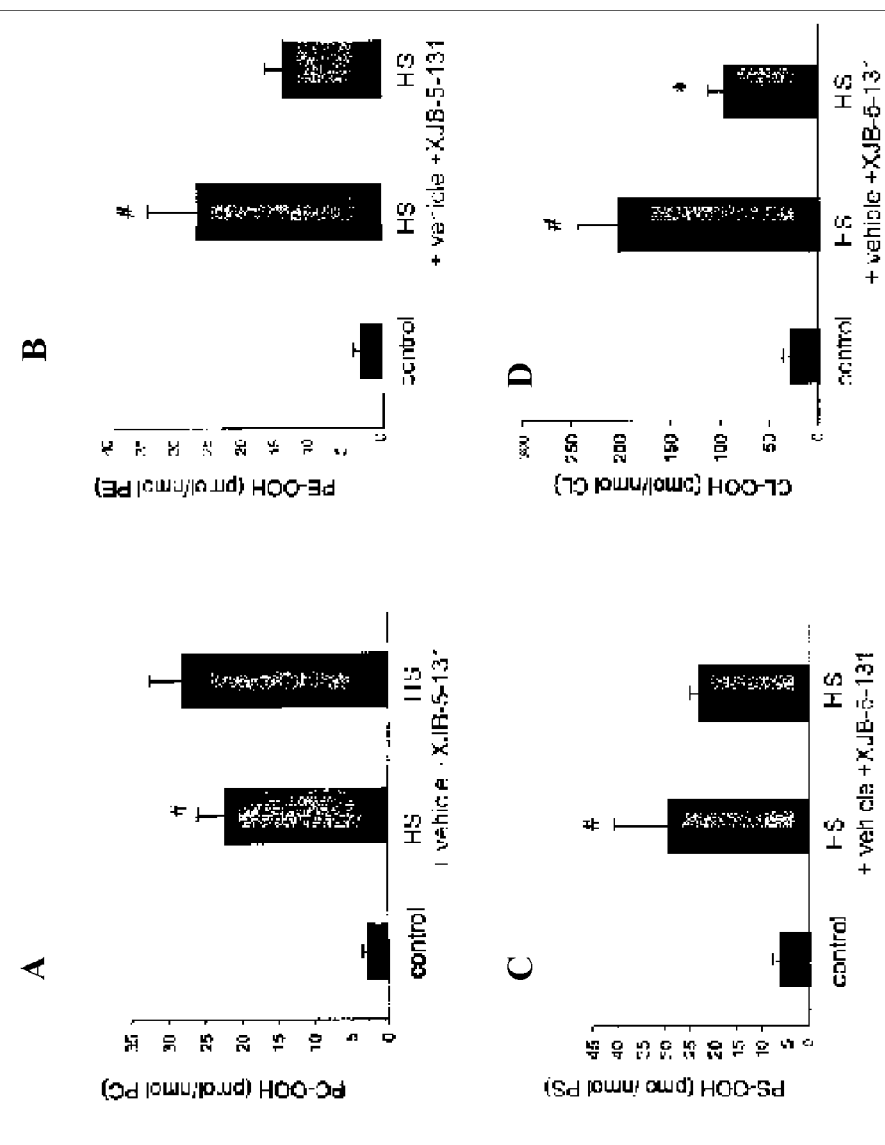
FIG. 6 illustrates the effects of intraluminal XJB-5-131 on hemorrhage-induced peroxidation of phospholipids in intestinal mucosa.

After two hours of HS, samples of ileal mucosa from the gut sacs filled with the vehicle and XJB-5-151 were obtained and compared with ileal mucosa of normal MECs. All samples were assayed with caspase 3 or caspase 7 activity as well as the peroxidation of phosphatidylcholine (PC), phosphatidylethanolamine (PE), phosphatidylserine (PS), and cardiolipin (CL), summarized in FIG. 6.

As can be seen in FIGS. 6A-6D, treatment with XJB-5-131 significantly ameliorated hemorrhage-induced peroxidation of CL, the only phospholipid tested found in mitochondria. However, treatment with XJB-5-131 only had a small effect on PE peroxidation and no effect on peroxidation of PC and PS. Based upon these trends, hemorrhagic shock is associated with substantial oxidative stress even in the absence of resuscitation. Further, this data also establishes that XJB-5-131 is an effective ROS scavenger as it localizes predominantly in mitochondria and protects CL from peroxidation.

Figure 7:
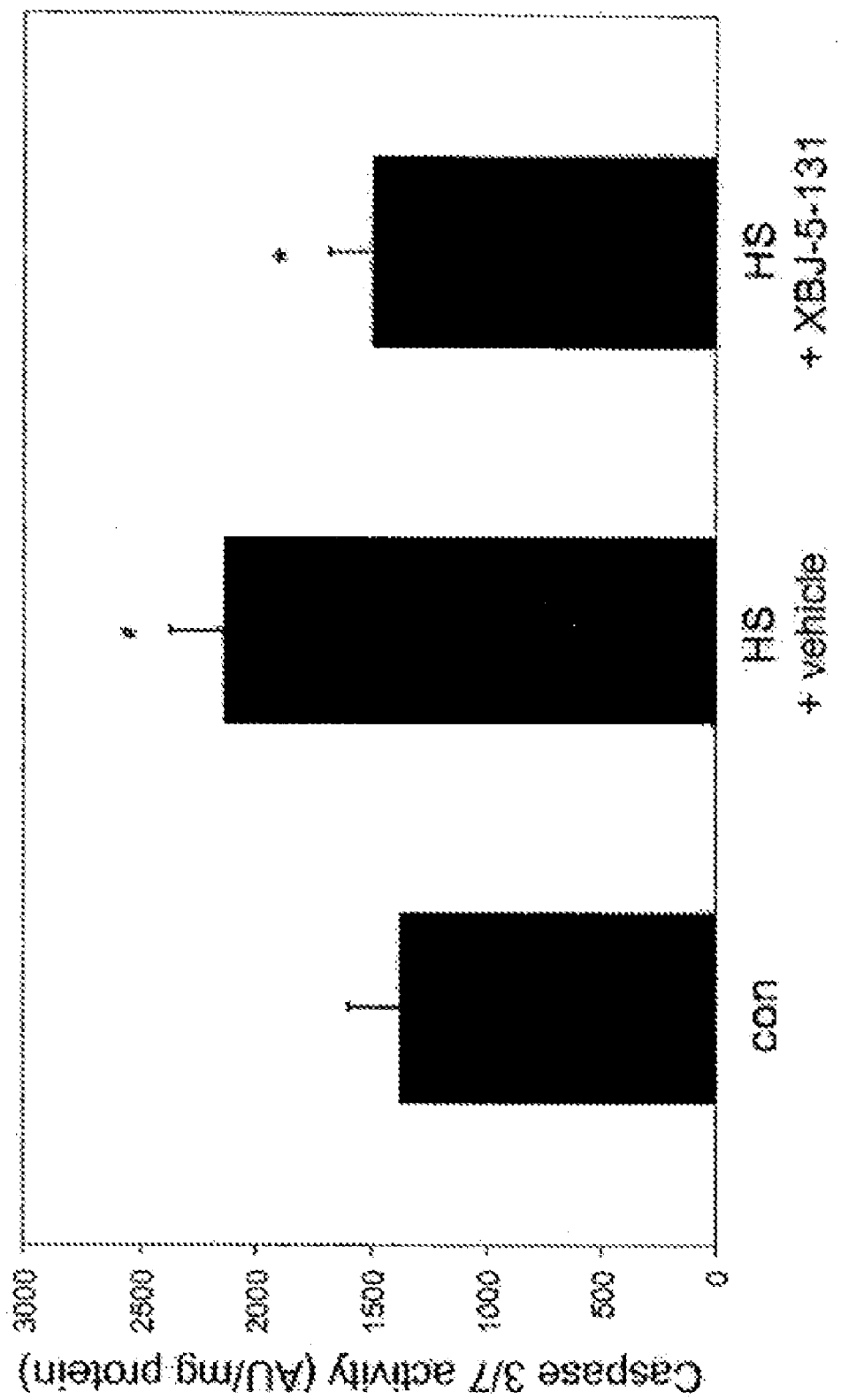
FIG. 7 is a graphical representation of caspase 3 and 7 activity that illustrates the effects of intraluminal XJB-5-131.

Relative to the activity measured in samples from normal animals, the activity of caspases 3 and 7 was markedly increased in vehicle-treated mucosal samples from hemorrhaged rats (FIG. 7). However, when the ileal segments were filled with XJB-5-131 solution instead of its vehicle, the level of caspase 3 and 7 activity after hemorrhagic shock was significantly decreased. Accordingly, hemorrhagic shock is associated with activation of pro-apoptotic pathways in gut mucosal cells. Moreover, our data support the view that this process is significantly ameliorated following mitochondrial treatment with XJB-5-131.

EXAMPLE III

In another series of experiments, monolayers of enterocyte-like cells, Caco-2$_{BBe}$, were studied for physiological and pathophysiological purposes for determining intestinal barrier function. Just as with the prior Example I and II with respect to ROS exposure, the permeability of Caco-2$_{BBE}$, monolayers increases when the cells are incubated with the ROS, hydrogen peroxide, or menadione (a redox-cycling quinine that promotes the formation of superoxide anion radicals), see Baker, R. D. et al., *Polarized Caco-2 cells, Effect of reactive oxygen metabolites on enterocyte barrierfunction*, DIGESTIVE DIS. SCI. 40:510-518 (1995); also Banan, A. et al., *Activation of delta-isoform ofprotein kinase C is required for oxidant-induced disruption of both the microtubule cytoskeleton and permeability barrier of intestinal epithelia*, J. PHARMACOL. EXP. THER. 303:17-28 (2002).

Figure 8:
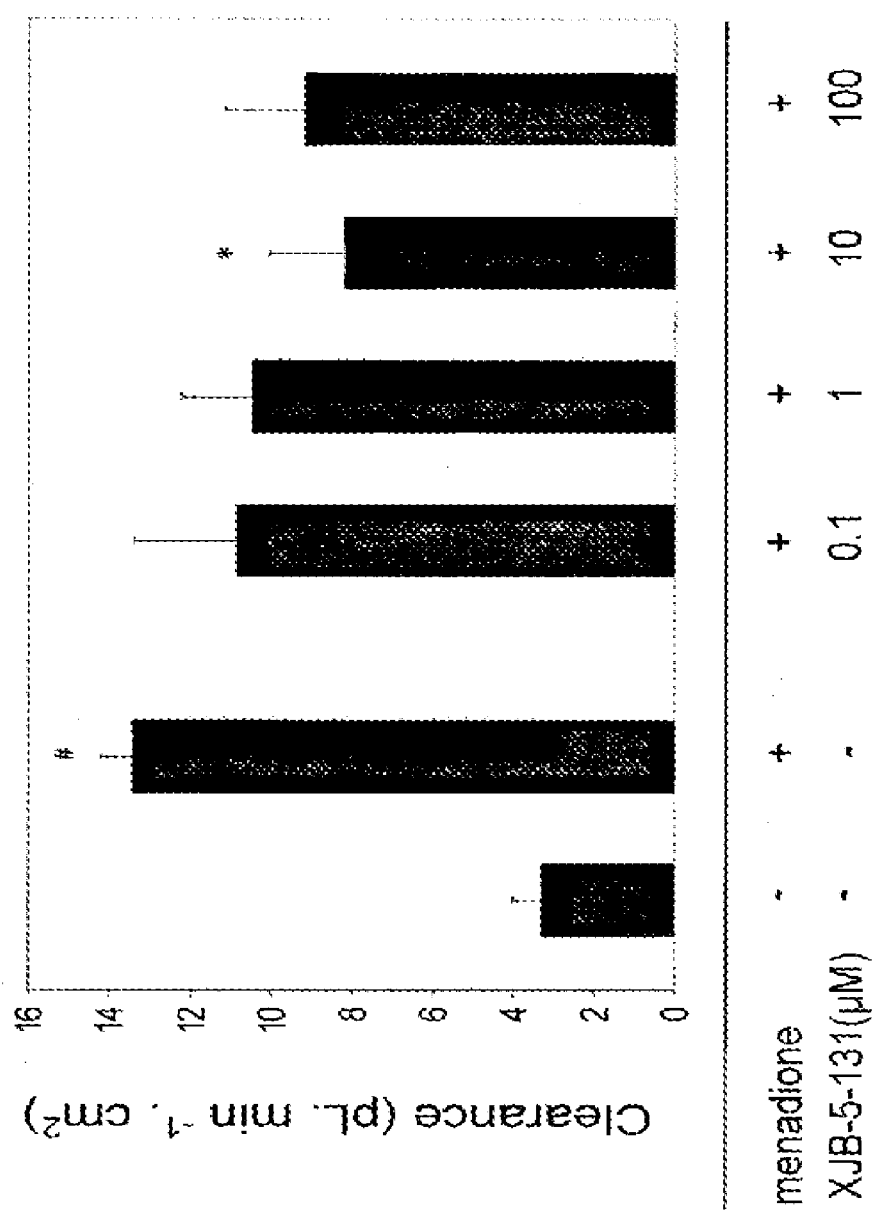
FIG. 8 is a graphical representation of permeability of XJB-5-131 with respect to Caco-2$_{BBe}$ human enterocyte-like monolayers subjected to oxidative stress. The permeability of the monolayers is expressed as a clearance ($pL \cdot h^{-1} \cdot cm^{-2}$).

Due to the results with respect to XJB-5-131 and its amelioration of hemorrhage-induced CL peroxidation in mucosal cells in vivo (see aforementioned Example I and II), a possible treatment using XJB-5-131 was investigated to determine if menadione-induced epithelial hyperpermeability could be ameliorated in vitro. Consistent with the prior in vivo observations, Caco-2$_{BBe}$ monolayers were incubated in the absence and in the presence of menadione, respectively. After 6 hours, incubation of Caco-2$_{BBe}$ monolayers with menadione caused a marked increase in the apical-basolateral clearance of FD4 (FIG. 8). Treatment with 10 µM XJB-5-131 provided significant protection against menadione-induced hyperpermeability. When the concentration of XJB-5-131 was increased to 100 µM, significant protection was no longer observed, suggesting that this compound has the potential to induce toxic effects at higher concentrations.

EXAMPLE IV

As reflected by the above in vivo and in vitro studies, XJB-5-131 had significantly beneficial effects on several biochemical and physiological read-outs. Accordingly, systemic administration of XJB-5-131 was investigated with respect to whether it would prolong survival of patients subjected to profound periods of hemorrhagic shock with massive blood loss in the absence of standard resuscitation with blood and crystalloid solution. As in the above studies, rats were utilized as test patients.

Sixteen rats were tested in this study. Following profound hemorrhagic shock consistent with the protocol described above for the prior studies, thirteen survived for at least 60 min and received the full dose of either XJB-5-131 solution or the vehicle, a 33:67 (v/v) mixture of DMSO and normal saline. Rats were treated with 2.8 ml/kg of vehicle or the same volume of XJB-5-131 solution during the final 20 min of the bleeding protocol. The total dose of XJB-5-131 infused was 2 µmol/kg. As shown in following Table 1, blood glucose, lactate and hemoglobin concentrations were similar in both groups at baseline and before and immediately after treatment; see data in table below. None of the between-group differences were statistically significant.

| Parameter | Compound | Baseline | End of first phase of hemorrage | End of second phase of hemorrage |
|---|---|---|---|---|
| Blood glucose concentration (mg/dL) | Vehicle | 143 ± 5 | 255 ± 30 | 219 ± 26 |
| | XJB-5-131 | 134 ± 4 | 228 ± 24 | 201 ± 38 |
| Blood lactate concentration (mEq/L) | Vehicle | 1.8 ± 0.4 | 606 ± 0.8 | 5.9 ± 1.3 |
| | XJB-5-131 | 1.8 ± 0.2 | 5.7 ± 0.8 | 5.6 ± 1.2 |
| Blood Hb concentration (g/dL) | Vehicle | 12.7 ± 0.5 | 11.1 ± 0.3 | 9.4 ± 0.2 |
| | XJB-5-131 | 12.7 ± 0.3 | 10.7 ± 0.3 | 9.4 ± 0.3 |

Figure 9A:
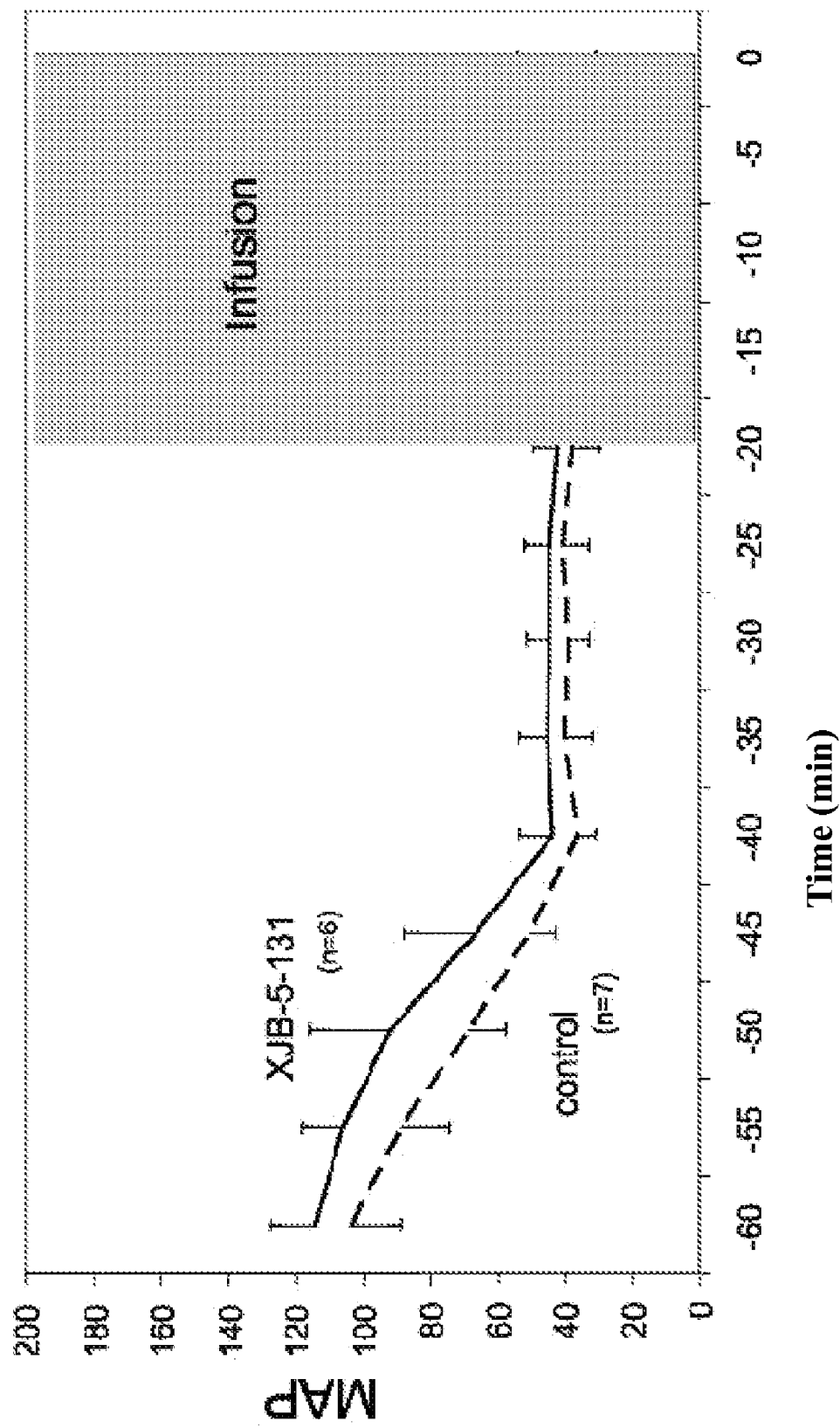
FIG. 9A is a graphical representation of the effects of intravenous treatment with XJB-5-131 on MAP (mean arterial pressure, mm Hg) of rates subjected to volume controlled hemorrhagic shock.
Figure 9B:
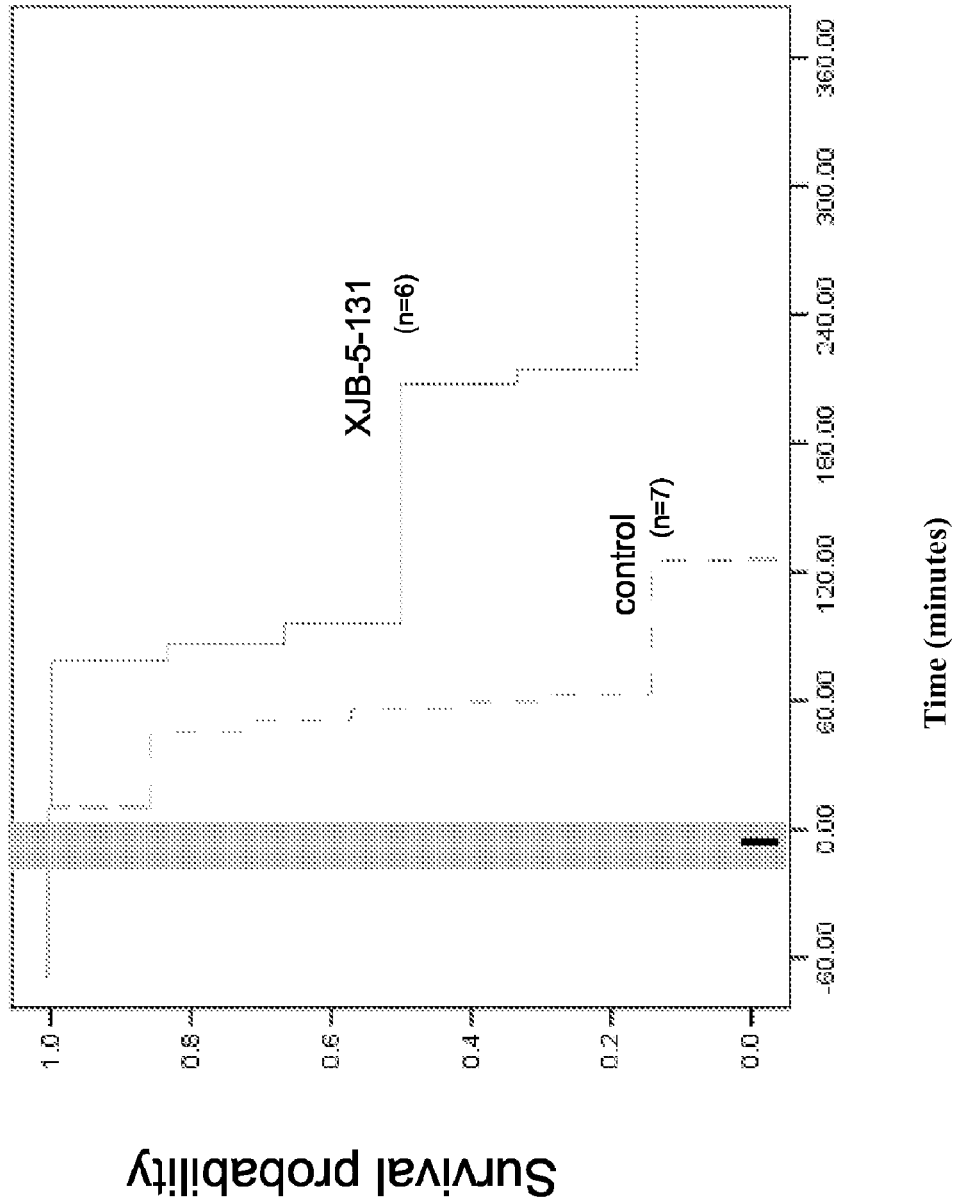
FIG. 9B is a graphical representation of the effects of intravenous treatment with XJB-5-131 on survival probability of rates subjected to volume controlled hemorrhagic shock.

In both groups, mean arterial pressure (MAP) decreased precipitously during the first phase of the hemorrhage protocol and remained nearly constant at 40 mm Hg during the beginning of the second phase. Shortly after treatment was started, MAP increased slightly in both groups (see FIG. 9A). Six of the seven animals in the vehicle-treated (control) group died within one hour of the end of the bleeding protocol and all were dead within 125 minutes (FIG. 9B). Rats treated with intravenous XJB-5-131 survived significantly longer than those treated with the vehicle. Three of the six rats survived longer than 3 hours after completion of the hemorrhage protocol; one rat survived the whole 6 hour post-bleeding observation period (FIG. 9B).

Analysis

Accordingly, analysis of the XJB-5-131 studies indicate that exposure of the patient to the compound prolongs the period of time that patients can survive after losing large quantities of blood due to traumatic injuries or other catastrophes (e.g., rupture of an abdominal aortic aneurysm).

By extending the treatment window before irreversible shock develops, treatment in the field with XJB-5-131 might "buy" enough time to allow transport of more badly injured patients to locations where definitive care, including control of bleeding and resuscitation with blood products and non-sanguinous fluids, can be provided. The results using a rodent model of hemorrhagic shock also open up the possibility that drugs like XJB-5-131 might be beneficial in other conditions associated with marked tissue hypoperfusion, such as stroke and myocardial infarction.

The results presented here also support the general concept that mitochondrial targeting of ROS scavengers is a reasonable therapeutic strategy. Although previous studies have shown that treatment with TEMPOL is beneficial in rodent HS situations (11);(12), a relatively large dose of the compound was required (30 mg/kg bolus+30 mg/kg per h). In contrast, treatment with a dose of XJB-5-131 that was about 300 fold smaller (~0.1 mg/kg) was clearly beneficial. The greater potency of XJB-5-131 as compared to TEMPOL presumably reflects the tendency of XJB-5-131 to localize in mitochondrial membranes, a key embodiment of the invention. As indicated in Example I, two hemigramicidin-4-$NH_2$-TEMPO conjugates (namely XJB-5-208 and XJB-5-131, see FIG. 2) are concentrated in the mitochondria of cultures mouse embryonic cells following incubation with solutions of the compounds.

Further, the use of XJB-5-131 significantly prolonged the survival of the rats subjected to massive blood loss, even though the animals were not resuscitated with either blood or other non-sanguinous fluids and they remained profoundly hypotensive.

In light of the above, synthetic hemigramicidin peptidyl-TEMPO conjugates permeate through the cell membrane and also the mitochondrial membrane where they act as free radical scavengers for reactive oxygen species ("ROS") such as, but not limited to, superoxide anion radicals. The conjugates are then reduced within the mitochondria by electron-transport proteins which are involved with the cellular respiration pathway, thereby coupling the decoupled ROS species. These conjugates also have the advantage, as discussed above, of being anti-apoptotic, especially in the case of compounds such as 5a and 5b.

By effectively reducing the amount of ROS species, a patient's condition, including an illness or other medical condition, may be ameliorated and, in some cases, survival may be prolonged as described in the Example IV study. Examples of such conditions, including diseases and other medical conditions, include (but are not limited to) the following medical conditions which include diseases and conditions: myocardial ischemia and reperfusion (e.g., after angioplasty and stenting for management of unstable angina or myocardial infarction), solid organ (lung liver, kidney, pancreas, intestine, heart) transplantation, hemorrhagic shock, septic shock, stroke, tissue damage due to ionizing radiation, lung injury, acute respiratory distress syndrome (ARDS), necrotizing pancreatitis, and necrotizing enterocolitis.

Whereas particular embodiments of this invention have been described above for purpose of illustration, it wiil be evident to those skilled in the art that numerous variations of the detials of the present invention may be made without departing from the invention as defined in the appended claims.

What is claimed is:
1. A compound selected from the group consisting of:
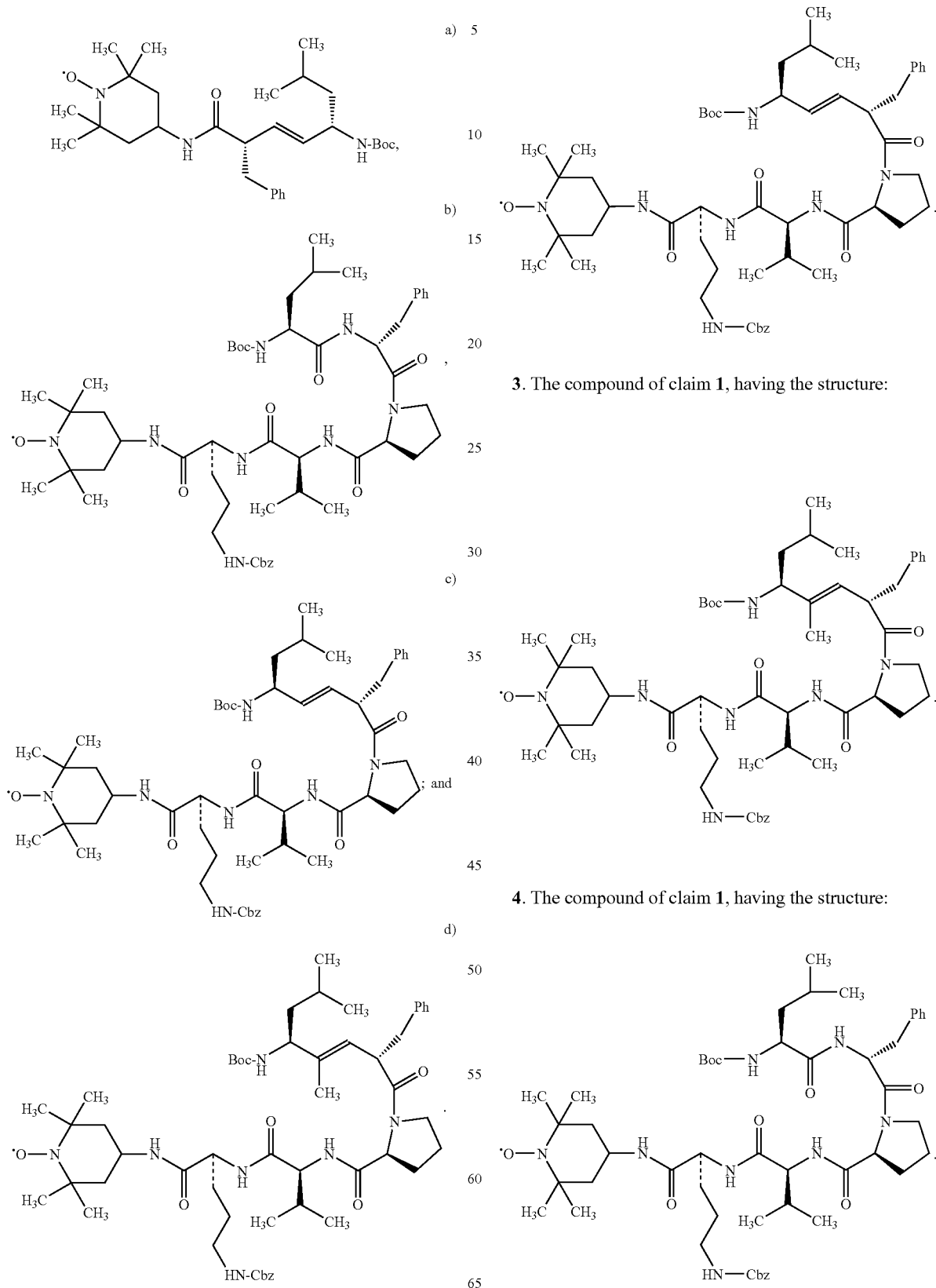
2. The compound of claim 1, having the structure:
3. The compound of claim 1, having the structure:
4. The compound of claim 1, having the structure:

5. The compound of claim 1, having the structure:

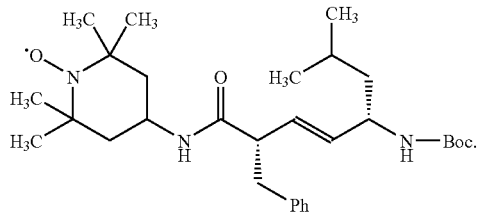

6. A compound for scavenging radicals in a mitochondrial membrane comprising a free radical scavenging group covalently linked to a membrane-targeting peptidyl fragment, the compound having the structure:

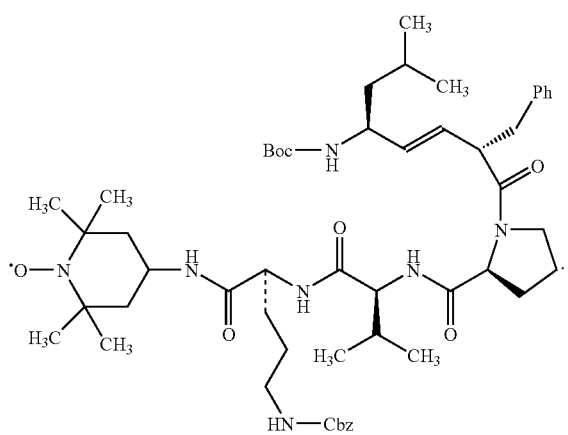

7. A method for delivering TEMPO to mitochondria comprising contacting the mitochondria with a compound selected from the group consisting of:

a)

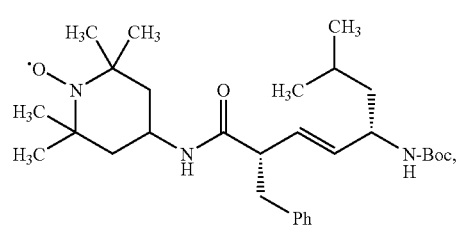

-continued b)

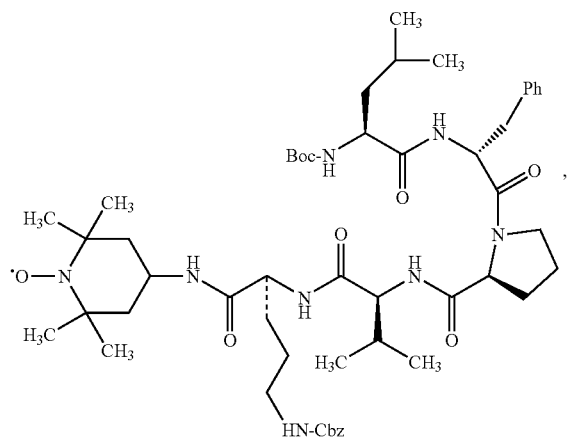

c)

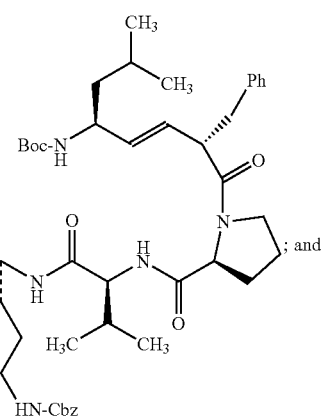

; and d)

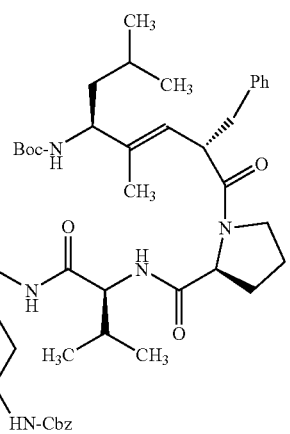

8. The method of claim 7, comprising delivering the compound to the mitochondria in an amount sufficient to scavenge reactive oxygen species.

9. The method of claim 7, wherein the compound is:

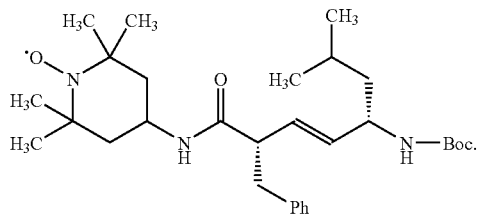

10. The method of claim 7, wherein the compound is:

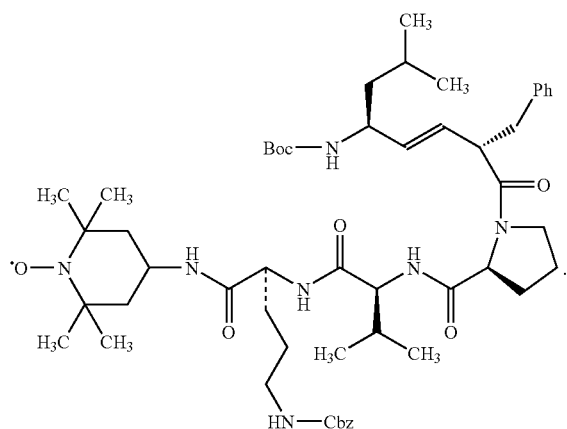

11. A method for therapeutically treating a patient having a condition associated with or caused by reactive oxygen species exposure comprising administering to said patient a compound selected from the group consisting of:

a)

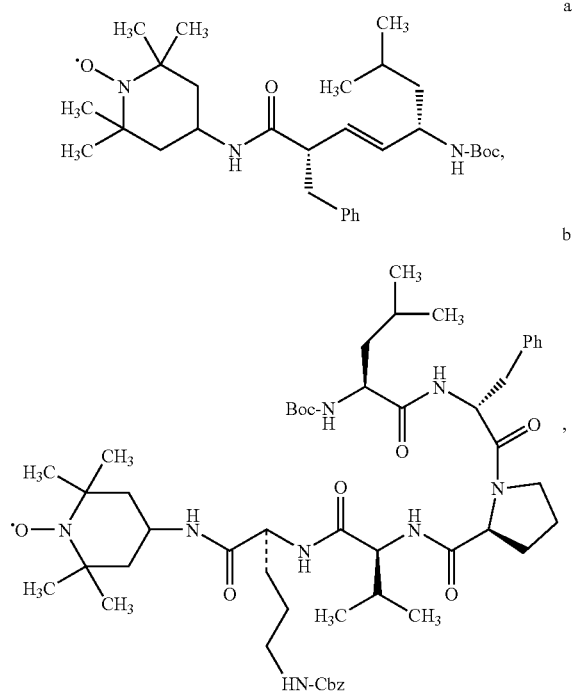

b)

c)

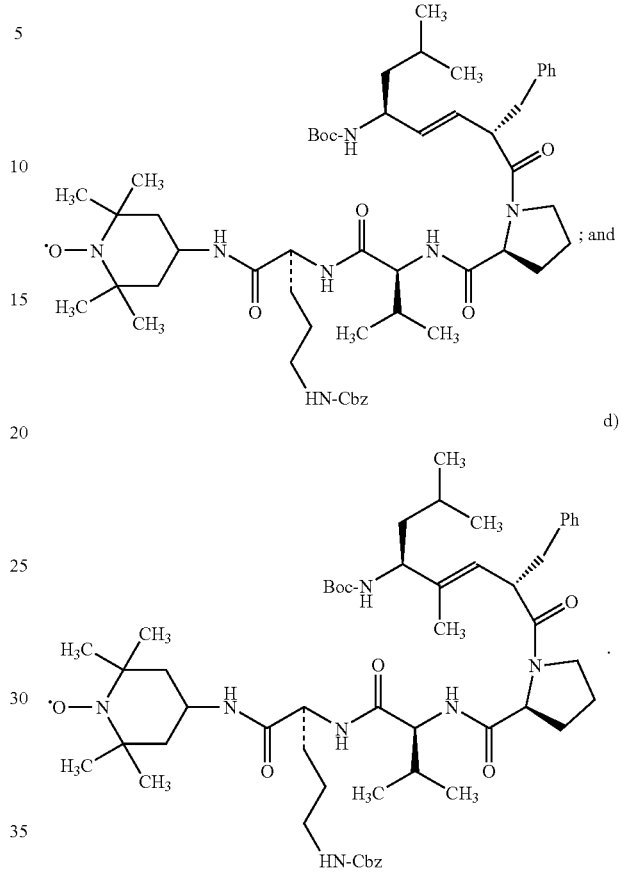

and d)

12. The method of claim 11, wherein said patient is a human being.

13. The method of claim 11, wherein said condition is hemorrhagic shock.

14. The method of claim 11, wherein said condition is selected from the group consisting of myocardial ischemia, myocardial reperfusion, solid organ transplantation, hemorrhagic shock, septic shock, stroke, tissue damage due to ionizing radiation, lung injury, acute lung injury, acute respiratory distress syndrome, necrotizing pancreatitis, and necrotizing enterocolitis.

15. A method for making the compound of claim 1, comprising:

a. Hydrozirconating an alkyne

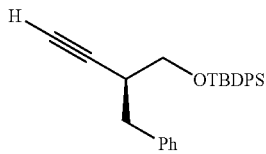

with $Cp_2ZrHCl$ to produce a first intermediate, transmetalating said alkyne with $Me_2Zn$, adding N-Boc-isovaleraldimine to produce a plurality of diastereomeric allylic amides, and desilylating and acylating said diastereomeric allylic amides to produce a second intermediate

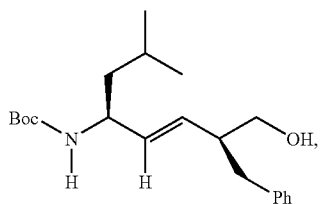

and
b. Oxidizing said second intermediate yielding a third intermediate

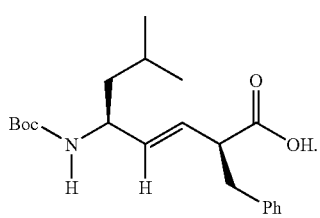

16. The method of claim 15, further coupling the third intermediate with 4-amino-TEMPO to produce

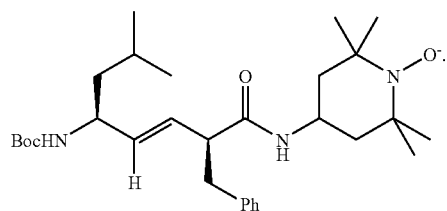

17. The method of claim 15, further comprising:
a. Coupling a tripeptide H-Pro-Val-Orn(Cbz)-OMe to the third intermediate using a coupling agent yielding a fourth intermediate:

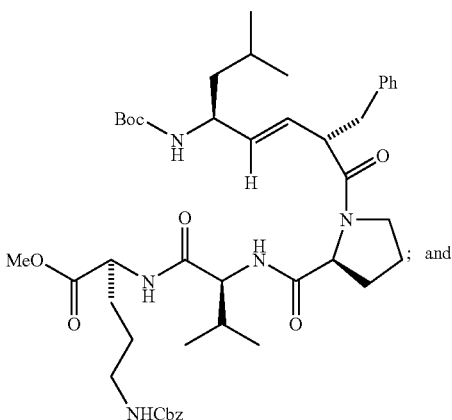

b. Saponifying the fourth intermediate and coupling with 4-amino-TEMPO to produce

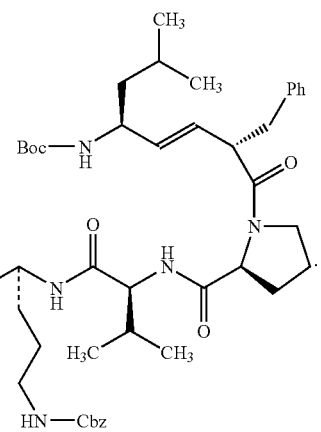

* * * * *